United States Patent
Wooley

(10) Patent No.: US 9,119,728 B2
(45) Date of Patent: Sep. 1, 2015

(54) REINFORCED CARBON FIBER/CARBON FOAM INTERVERTEBRAL SPINE FUSION DEVICE

(75) Inventor: Paul Hastings Wooley, Wichita, KS (US)

(73) Assignee: CIBOR, INC., Wichita, KS (US)

( * ) Notice: Subject to any disclaimer, the term of this patent is extended or adjusted under 35 U.S.C. 154(b) by 777 days.

(21) Appl. No.: 13/351,578

(22) Filed: Jan. 17, 2012

(65) Prior Publication Data

US 2012/0185047 A1    Jul. 19, 2012

Related U.S. Application Data

(60) Provisional application No. 61/433,450, filed on Jan. 17, 2011.

(51) Int. Cl.
*A61F 2/44* (2006.01)
*A61F 2/30* (2006.01)
*A61F 2/28* (2006.01)

(52) U.S. Cl.
CPC ............... *A61F 2/4455* (2013.01); *A61F 2/44* (2013.01); *A61F 2/4465* (2013.01); *A61F 2/30965* (2013.01); *A61F 2002/2817* (2013.01); *A61F 2002/2835* (2013.01); *A61F 2002/30034* (2013.01); *A61F 2002/30062* (2013.01); *A61F 2002/3092* (2013.01); *A61F 2002/3093* (2013.01); *A61F 2002/30331* (2013.01); *A61F 2002/30448* (2013.01); *A61F 2002/30451* (2013.01); *A61F 2002/30576* (2013.01); *A61F 2002/30677* (2013.01); *A61F 2002/30772* (2013.01); *A61F 2002/30785* (2013.01); *A61F 2002/30795* (2013.01);

(Continued)

(58) Field of Classification Search
USPC .......................... 623/17.16; 427/2.26
See application file for complete search history.

(56) References Cited

U.S. PATENT DOCUMENTS

| 4,070,514 A | 1/1978 | Eatherly et al. |
| 4,978,358 A | 12/1990 | Bobyn |
| 5,282,861 A * | 2/1994 | Kaplan ..................... 623/23.51 |

(Continued)

OTHER PUBLICATIONS

Pec, Martina K., et al., "Reticulated Vitreous Carbon: A Useful Material for Cell Adhesion and Tissue Invasion", European Cells and Materials, vol. 20m 2010 pp. 282-294 (13 pages).

(Continued)

*Primary Examiner* — Christian Sevilla
(74) *Attorney, Agent, or Firm* — Hovey Williams LLP

(57) ABSTRACT

An intervertebral implant for placement in the intervertebral space between two adjacent vertebral bodies is provided. The implant comprises a hollow cage and a porous core received within the cage. The cage comprises a superior surface configured to contact a first vertebral body, an inferior surface configured to contact a second vertebral body, and an outer wall extending between the superior surface and inferior surface. The outer wall comprises an exterior surface defining the outer perimeter of the implant, and an interior surface defining an inner (hollow) space or void. The porous core is received within the inner space or void, and preferably fills the void. The core comprises a carbonaceous matrix comprising a continuous phase having a surface and defining a plurality of open spaces throughout said matrix. Suitable carbonaceous matrices are selected from the group consisting of carbon foam, graphite foam, and combinations thereof. Methods of making and using the same, along with kits to facilitate such use are also provided.

19 Claims, 17 Drawing Sheets

(52) U.S. Cl.
    CPC .......... *A61F 2002/30843* (2013.01); *A61F 2002/4475* (2013.01); *A61F 2310/00161* (2013.01)

(56) References Cited

U.S. PATENT DOCUMENTS

| | | | |
|---|---|---|---|
| 5,865,845 A * | 2/1999 | Thalgott | 623/17.16 |
| 5,888,469 A | 3/1999 | Stiller et al. | |
| 5,989,289 A * | 11/1999 | Coates et al. | 623/17.16 |
| 6,039,762 A * | 3/2000 | McKay | 623/17.11 |
| 6,103,149 A | 8/2000 | Stankiewicz | |
| 6,143,033 A | 11/2000 | Paul et al. | |
| 6,187,047 B1 | 2/2001 | Kwan et al. | |
| 6,277,149 B1 * | 8/2001 | Boyle et al. | 623/17.16 |
| 6,346,123 B1 | 2/2002 | McKay | |
| 6,660,038 B2 | 12/2003 | Boyer et al. | |
| 6,846,327 B2 | 1/2005 | Khandkar et al. | |
| 6,974,625 B2 * | 12/2005 | Hunter et al. | 428/304.4 |
| 7,044,972 B2 | 5/2006 | Mathys et al. | |
| 7,229,477 B2 | 6/2007 | Biscup | |
| 7,232,464 B2 | 6/2007 | Mathieu et al. | |
| 7,303,583 B1 | 12/2007 | Schar et al. | |
| 7,401,643 B2 | 7/2008 | Queheillalt et al. | |
| 7,500,991 B2 | 3/2009 | Bartish et al. | |
| 7,563,284 B2 | 7/2009 | Coppes et al. | |
| 7,637,950 B2 | 12/2009 | Baccelli et al. | |
| 7,846,207 B2 | 12/2010 | Lechmann et al. | |
| 7,871,441 B2 | 1/2011 | Eckman | |
| 7,959,941 B2 | 6/2011 | Knaack et al. | |
| 7,964,206 B2 | 6/2011 | Suokas et al. | |
| 7,968,026 B1 | 6/2011 | Teoh et al. | |
| 7,968,111 B2 | 6/2011 | Pavesio et al. | |
| 8,025,896 B2 | 9/2011 | Malaviya et al. | |
| 2001/0016775 A1 * | 8/2001 | Scarborough et al. | 623/17.16 |
| 2002/0016633 A1 * | 2/2002 | Lin et al. | 623/17.11 |
| 2002/0026243 A1 * | 2/2002 | Lin | 623/17.11 |
| 2002/0029082 A1 * | 3/2002 | Muhanna | 623/17.11 |
| 2003/0028249 A1 | 2/2003 | Baccelli et al. | |
| 2003/0105527 A1 * | 6/2003 | Bresina | 623/17.16 |
| 2003/0125739 A1 * | 7/2003 | Bagga et al. | 606/61 |
| 2004/0138754 A1 | 7/2004 | Lang et al. | |
| 2004/0193270 A1 | 9/2004 | DiMauro | |
| 2004/0230306 A1 | 11/2004 | Hoeck et al. | |
| 2005/0049706 A1 | 3/2005 | Brodke et al. | |
| 2005/0177237 A1 | 8/2005 | Shappley et al. | |
| 2005/0177245 A1 | 8/2005 | Leatherbury et al. | |
| 2005/0228498 A1 | 10/2005 | Andres | |
| 2006/0188542 A1 | 8/2006 | Bobyn et al. | |
| 2006/0271201 A1 | 11/2006 | Kumar et al. | |
| 2007/0270953 A1 | 11/2007 | Trieu | |
| 2008/0206297 A1 | 8/2008 | Roeder et al. | |
| 2009/0248047 A1 | 10/2009 | Marrs et al. | |
| 2010/0255053 A1 | 10/2010 | Savage-Erickson | |
| 2010/0305704 A1 | 12/2010 | Messerli et al. | |

OTHER PUBLICATIONS

Loguidice, Vito A. et al, "Anterior Lumbar Interbody Fusion," Spine, 1988, vol. 13, No. 3, pp. 366-369.

Lin, Paul et al., "Posterior Lumbar Interbody Fusion.," Clinical Orthopaedics and Related Research, Nov. 1983, vol. 180, pp. 154-168.

Mayer, H. Michael, "The ALIF Concept," Eur Spine J, 2000, 9 (Suppl 1) S35-S43.

Jacobs, Wilco et al., "Fusion for Low-Grade Adult Isthmic Spondylolisthesis: a Systematic Review of the Literature," Eur Spine J, 2006, 15: 391-402.

Walter, Jan et al., "PEEK Cages as a Potential Alternative in the Treatment of Cervical Spondylodiscitis: a Preliminary Report on a Patient Series," Eur Spine J, 2010, 19:1004-1009.

Takahashi, Hiroshi et al., "Effect of Cage Geometry on Sagittal Alignment after Posterior Lumbar Interbody Fusion for Degenerative Disc Disease," Journal of Orthopaedic Surgery, 2010, 18(2):139-42.

Yu, H. Y. et al., "Osteoblast Colonization of Biomimetic Carbon Foam Scaffolds," Poster No. 1270A, 56th Annual Meeting of the Orthopaedic Research Society.

Chang-Jung, Chiang et al., "Anterior Cervical Fusion Using a Polyetheretherketone Cage Containing a Bovine Xenograftp," Spine, 2008, vol. 33, No. 23, pp. 2524-2428.

Lee, Jae Hyup, "Fusion Rates and Subsidence of Morselized Local Bone Grafted in Titanium Cages in Posterior Lumbar Interbody Fusion Using Quantitative Three-Dimensional Computed Tomography Scans," Spine, 2010, vol. 35, No. 15, pp. 1460-1465.

Roeder, et al., "HA Whisker Reinforced PEKK Implants," Adv. Mater. Process, 2009, abstract only.

Karpinski et al., "Posterior Lumbar Interbody Fusion and Cages," Chir Narzadow Ruchu Ortop Pol., 1999, 64(4): 463-70, abstract only.

Wooley et al., "Inflammatory Responses to Orthopaedic Biomaterials in the Murine Air Pouch," Biomaterials, Jan. 2002, 23(2): 517-26, abstract only.

Ottaviani et al, "Inflammatory and Immunological Responses to Hyaluronan Preparations. Study of a Murine Biocompatibility Model," J Bone Joint Surg Am, Jan. 2007, 89(1): 148-57, abstract only.

http://www.stryker.com/en-us/products/Spine/InterbodyVertebralBodyReplacement/AVSASPEEKSpacerImplant/index.htm Product Description Stryker AVS AS PEEK Spacer Implant, Accessed Aug. 2011.

http://www.stryker.com/en-us/products/Spine/InterbodyVertebralBodyReplacement/AVSALPEEKSpacerImplant/index.htm Product Description Stryker AVS AL PEEK Spacer Implant, Accessed Aug. 2011.

http://synthes.vo.llnwd.net/o16/Mobile/Synthes%20North%20America/Product%20Support%20Materials/Product%20Information%20Sheets/SPINE/SPPISSynCgOpenJ4451D.pdf Product Description SynCage—Vertical Body Replacement Device (Ti), 2003.

http://synthes.vo.llnwd.net/o16/Mobile/Synthes%20North%20America/Product%20Support%20Materials/Brochures/SPINE/SPBROVertSpc-ARJ4143G.pdf Product Description SynCage—Vertical Body Replacement Device (PEEK), 2006.

http://synthes.vo.llnwd.net/o16/Mobile/Synthes%20North%20America/Product%20Support%20Materials/Technique%20Guides/SPINE/SPTGSynFix-LRJ7022H.pdf Product Description SynFix-LR System—ALIF, 2008.

http://www.depuy.com/healthcare-professionals/product-details/cougar-system?s=search_13134535801430940&i=13&consulta=t&keyword=&company=250&specialty=0&category=0&focus=0&family=0&sorting=title&sorting_type=asc&page=1&per_page=100 Product Description Lumbar Degenerative CougarTM System, Accessed Aug. 2011.

http://www.stryker.com/en-us/products/Spine/InterbodyVertebralBodyReplacement/Implant/index.htm Product Description Stryker Unite—ALIF Implant, Accessed Aug. 2011.

http://www.medtronic.com/health-consumers/lumbar-degenerative-disc-disease/surgery/our-spinal-fusion-product/infuse/index.htm Product Description Infuse Bone Graft and the LT-Cage Device, Accessed Aug. 2011.

http://www.depuy.com/healthcare-professionals/product-details/devex-system?s=search_13134535801430940&i=14&consulta=t&keyword=&company=250&specialty=0&category=0&focus=0&family=0&sorting=title&sorting_type=asc&page=1&per_page=100 Product Description Lumbar Degenerative DEVEX® System, Accessed Aug. 2011.

http://www.depuy.com/healthcare-professionals/product-details/leopard-system?s=search_13134535801430940&i=32&consulta=t&keyword=&company=250&specialty=0&category=0&focus=0&family=0&sorting=title&sorting_type=asc&page=1&per_page=100 Product Description Lumbar Degenerative LEOPARD® System, Accessed Aug. 2011.

http://www.stryker.com/en-us/products/Spine/InterbodyVertebralBodyReplacement/AVSTLPEEKSpacerImplant/index.htm Product Description Stryker AVS TL Peek Spacer Implant, Accessed Aug. 2011.

http://www.depuy.com/healthcare-professionals/product-details/lt-mesh-st-mesh-implant?s=search_13134535801430940&i=33

(56) References Cited

OTHER PUBLICATIONS

&consulta=t&keyword=&company=250&specialty=0&category=0&focus=0&family=0&sorting=title&sorting_type=asc&page=1&per_page=100 Product Description Lumbar Degenerative LT Mesh & ST Mesh Implants, Accessed Aug. 2011.
www.depuy.com/healthcare-professionals/product-details/concorde-bullet-system?s=search_1313435801430940&i=10&consulta=t&keyword=&company=250&specialty=0&category=0&focus=0&family=0&sorting=title&sorting_type=asc&page=1&per_page=100 Product Description Minimally Invasive Surgery (MIS) CONCORDETM Bullet System, Accessed Aug. 2011.
www.depuy.com/healthcare-professionals/product-details/jaguar-lumbar-if-cage-system?ssearch_1313435801430940&i=29&consulta=t&keyword=&company=250&specialty=0&category=0&focus=0&family= 0&sorting=title&sorting_type=asc&page=1&per_page=100 Product Description Lumbar Degenerative Jaguar Lumbar I/F Cage, Accessed Aug. 2011.
http://www.depuy.com/healthcare-professionals/product-details/saber-lumbar-if-cage-system?s=search_1313435801430940&i=48&consulta=t&keyword=&company=250&specialty=0&category=0&focus=0&family=0&sorting=title&sorting_type=asc&page=1&per_page=100 Product Description Lumbar Degenerative SABERTM Lumbar I/F Cage® System, Accessed Aug. 2011.
http://www.stryker.com/en-us/products/Spine/InterbodyVertebralBodyReplacement/RTF-PLIFmplant/index.htm Product Description RTF-PLIF Implant Ray Threaded Fusion Cage PLIF, Accessed Aug. 2011.
http://stryker.com/en-us/products/Spine/InterbodyVertebralBodyReplacement/AVSPLPEEKSpacerImplant/index.htm Product Description Stryker AVS PL PEEK Spacer Implant, Accessed Aug. 2011.
http://depuy.com/healthcare-professionals/product-details/surgical-titanium-mesh-implants?s=search_1313435801430940&i=57&consulta=t&keyword=&company=250&specialty=0&category=0&focus=0&family=0&sorting=title&sorting_type=asc&page=1&per_page=100 Product Description Lumbar Degenerative, Thoraco Lumbar Trauma Surgical Titanium Mesh Implants, Accessed Aug. 2011.
http://depuy.com/healthcare-professionals/product-details/ocelot-stackable-cage-system?s=search_1313435801430940&i=41&consulta=t&keyword=&company=250&specialty=0&category=0&focus=0&family=0&sorting=title&sorting_type=asc&page=1&per_page=100 Product Description Lumbar Degenerative, Thoraco Lumbar Trauma Ocelottm Stackable Cage System, Accessed Aug. 2011.
http://globusmedical.com/index.php?option=com_k2&view=item&layout=item&id=225&Itemid=318 Product Description Independence®, plate and space system, Feb. 26, 2009.
http://globusmedical.com/index.php?option=com_k2&view=item&layout=item&id=219&Itemid=318 Product Description Continental®, lumbar interbody fusion device, Accessed Aug. 2011.
http://www.innovasis.com/thorac-lumbar.htm Product Description A-Box(R), Accessed Aug. 2011.
http://globusmedical.com/index.php?option=com_k2&view=item&layout=item&id=259&Itemid=4 Product Description Sustain® Sustain-R Medium, Accessed Aug. 2011.
http://globusmedical.com/index.php?option=com_k2&view=item&layout=item&id=258&Itemid=4 Product Description Sustain® Sustain-R Large, Accessed Aug. 2011.
Wiesling, "Carbon Fibre reinforced PEEK medical Implants," European Cells and Materials, 2008, vol. 16, Suppl. 2, p. 8.
Search Report and Written Opinion dated Jul. 2, 2012 in corresponding PCT/US2012/021509 filed on Jan. 17, 2012.
International Search Report and Written Opinion dated May 23, 2012, in related PCT/US2011/056155 filed on Oct. 13, 2011.
Ultramet Advanced Materials Solutions, Refractory Open-Cell Foams: Carbon, Ceramic, and Metal, http://www.ultramet.com/refractoryopencells_rvcf.html.
ULTRAMET—Refractory Open-Cell Foams: Carbon, Ceramic, and Metal: Reticulated Vitreous Carbon Foam, http://www.ultramet.com/refractoryopencells_properites_of_foam.html.
Fauber, "Infuse cited in patients' painful bone overgrowth," JSOnline, Jun. 27, 2011, http://www.jsonline.com/watchdog/watchdogreports/124630959.html.
ERG Materials and Aerospace Corporation, Reticulated Vitreous Carbon: A New Form of Carbon, http://www.ergaerospace.com.
Medtronic INFUSE® Bone Graft + LT-CAGE® Lumbar Tapered Fusion Device Fact Sheet, 2011, http://wwwp.medtronic.com.
Turgut, "Pore structure engineering for carbon foams as possible bone implant material," J. Biomed Mater Res A, Jun. 1, 2008;85(3):588-96.
Office Action dated Feb. 25, 2013 in related U.S. Appl. No. 13/272,793, filed Oct. 13, 2011.
Office Action dated Jun. 5, 3012 in related U.S. Appl. No. 13/272,793, filed Oct. 13, 2011.

\* cited by examiner

A. Naive carbon foam  B. Albuin coated carbon foam
C. Phosphate coated carbon foam  D. Hydroxyapatite coated carbon foam A. Open Cell Carbon Foam  B. Closed Cell Carbon Foam

*p<0.05

REINFORCED CARBON FIBER/CARBON FOAM INTERVERTEBRAL SPINE FUSION DEVICE

CROSS-REFERENCE TO RELATED APPLICATIONS

The present application claims the priority benefit of U.S. Provisional Patent Application Ser. No. 61/433,450, filed Jan. 17, 2011, entitled Reinforced Carbon Fiber/Carbon Foam Composite Intervertebral Spine Fusion Device, incorporated by reference in its entirety herein.

BACKGROUND OF THE INVENTION

1. Field of the Invention

The present invention relates to improved intervertebral implants for spinal fusion.

2. Description of Related Art

Current spine procedures for treating damaged or diseased intervertebral discs are critically dependent upon achieving interbody fusion—the replacement of the diseased disc with a spacer that allows bone growth to fuse the adjacent vertebral bodies. Titanium cages or PEEK spacers containing autograft or allograft bone are currently utilized to achieve this medical outcome, but are frequently unsuccessful due to a poor rate of bone growth that fails to achieve complete fusion. A systematic review of the literature reveals that anterior interbody fusion rates vary from 47% to 90%, suggesting a less than excellent fusion rate with current technology. Titanium cages appear to provide insufficient lordotic angle and the fused area of local bone inside cages at regions exposed to endplates is insufficient for physiologic load transmission. PEEK devices appear to represent a reasonable alternative but a thick wall construct is required using PEEK to provide sufficient biomechanical strength during the fusion process. The volume of the solid PEEK insert cannot be replaced by bone, as this biomaterial is not degradable and remains within the body indefinitely. Thus, the overall volume of the new bony column is decreased, contributing to less stability and strength. Existing devices also suffer from problems of subsidence into the adjacent vertebral bodies over time.

Thus, there remains a need in the art for intervertebral implants that promote successful interbody fusion and avoid problems of subsidence seen in existing devices.

SUMMARY OF THE INVENTION

The invention overcomes problems encountered in previous implants by providing an intervertebral implant comprising a cage and a porous core. The cage comprises a superior surface, an inferior surface, and an outer wall extending between the superior surface and inferior surface. The outer wall comprises an exterior surface defining the outer perimeter of the implant, and an interior surface defining an inner space. The porous core is received within this inner space. The core comprises a carbonaceous matrix comprising a continuous phase having a surface and defining a plurality of open spaces throughout the matrix.

The invention also provides a method of making an intervertebral implant. The method comprises providing a precursor structure that comprises a cage and a porous core. The cage comprises a superior surface, an inferior surface, and an outer wall extending between the superior surface and inferior surface. The outer wall comprises an exterior surface defining the outer perimeter of the implant, and an interior surface defining an inner space. The porous core is received within this inner space. The core comprises a carbonaceous matrix comprising a continuous phase having a surface and defining a plurality of open spaces throughout the matrix. In the method, a coating is formed adjacent the continuous phase surface of the matrix. The coating is selected from the group consisting of osteopromotive materials, therapeutic agents, and combinations thereof.

A method of replacing an intervertebral disc in an interbody space between first and second vertebral bodies of a subject is also provided. The method comprises providing an intervertebral implant comprising a cage and a porous core, shaping the porous core to yield a void, packing said void with a bone grafting material, and implanting the implant into the interbody space of the subject between the first and second vertebral bodies. The implant cage comprises a superior surface, an inferior surface, and an outer wall extending between the superior surface and inferior surface. The outer wall comprises an exterior surface defining the outer perimeter of the implant, and an interior surface defining an inner space. The porous core is received within this inner space. The core comprises a carbonaceous matrix comprising a continuous phase having a surface and defining a plurality of open spaces throughout the matrix.

The invention also provides a kit for use in replacing an intervertebral disc in an interbody space between first and second vertebral bodies of a subject. The kit comprises an intervertebral implant and instructions for the implantation thereof into the subject. The implant comprises a cage and a porous core. The cage comprises a superior surface, an inferior surface, and an outer wall extending between the superior surface and inferior surface. The outer wall comprises an exterior surface defining the outer perimeter of the implant, and an interior surface defining an inner space. The porous core is received within this inner space. The core comprises a carbonaceous matrix comprising a continuous phase having a surface and defining a plurality of open spaces throughout the matrix.

DETAILED DESCRIPTION

The following sets forth the invention with reference to the preferred embodiments illustrated in the Figures. It is to be understood, however, that these preferred embodiments are provided by way of example and nothing therein should be taken as a limitation upon the overall scope of the invention that is claimed. The various embodiments depicted in the Figures and described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

In more detail, the present invention provides implants for replacing collapsed, damaged, diseased, or otherwise unstable intervertebral discs that have been partially or totally resected or excised from the vertebra. The intervertebral implants help restore the height of adjacent vertebral bodies as well as the natural curvature (lordotic/kyphotic angle) and sagittal alignment of the spine. The inventive implants resist subsidence into adjacent vertebral bodies by promoting bony "through growth" for more complete fusion, which permits the fused bone to ultimately bear the compressive forces of the subject's body instead of the implant cage. However, it has been found that a small degree if initial subsidence may actually be beneficial to enhancing contact with adjacent vertebral bodies and creating comprehensive fusion of the vertebral bodies. It will be appreciated that the bony through growth results in a bony column that prevents further subsidence of the implant into adjacent bone.

Figure 1:
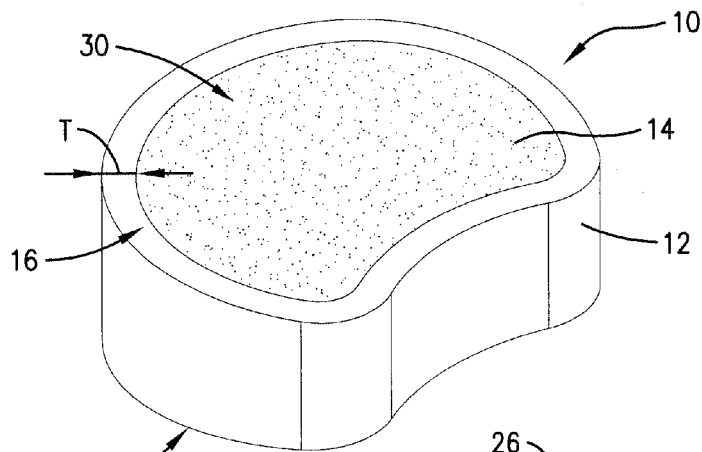
FIG. 1 is an isometric view of an intervertebral implant in accordance with one or more embodiments of the invention.
Figure 2:
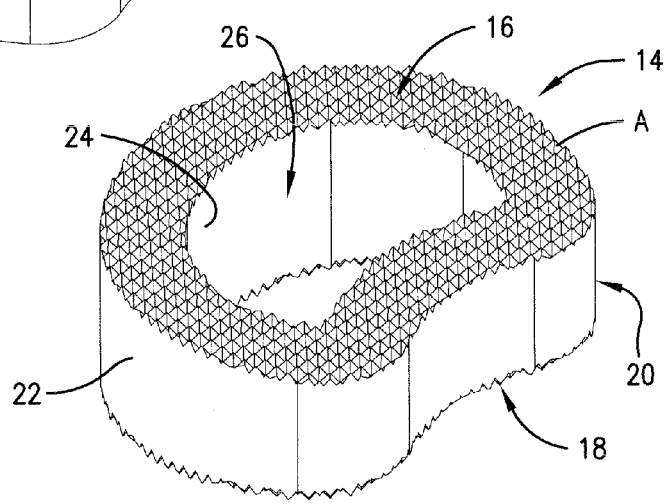
FIG. 2 is an isometric view of the implant cage in accordance with one or more embodiments of the invention.

With reference to FIG. 1, the implant 10 comprises a three-dimensional cage 12 and a porous core 14. The implant 10 can be configured for use at any location in the spine from C3 to L4 to replace a damage intervertebral disc. The cage 12 is formed from carbon fiber reinforced polymer. More preferably, the cage 12 is formed of a carbon fiber weave impregnated and fused with a polymeric matrix. The carbon fiber can be short-strand or long-strand, although long-strand carbon fiber is particularly preferred for use in the invention. Suitable polymers include poly-ether-ether-ketone (PEEK), poly-ether-ketone-ketone (PEKK), or combinations thereof. The cage 12 can be formed using traditional thermoplastic processing methods, including injection molding, extrusion, infusion/impregnation, compression molding, and combinations thereof. The cage 12 is preferably an integrally formed hollow body. As used herein, "integrally formed" means formed of a continuous, uniform material, as a single piece, throughout, and expressly excludes structures that are formed by attaching or joining multiple pieces together (including welding, bonding, or other permanent attachment techniques). It will be appreciated that the tangent lines shown in the Figures simply indicate the contours of the implant and not seams where multiple pieces were fit together. As illustrated in FIG. 2, the cage 12 comprises a superior surface 16, and an inferior surface 18, and an outer wall 20 extending between the superior surface 16 and inferior surface 18. The superior 16 and inferior 18 surfaces of the cage 12 are configured to interface with the endplates of adjacent vertebral bodies 40 when the implant 10 is inserted into the interbody space 42 (see FIG. 10). The superior 16 and inferior 18 surfaces may each optionally include teeth, protrusions, or other surface roughness 19 to prevent expulsion of the implant device and provide initial stability. The outer wall 20 has an exterior surface 22 which defines the outer perimeter of the cage 12, and correspondingly the implant 10, and an interior surface 24 which defines an inner space 26 or chamber of the hollow body. The inner space 26 extends axially through the cage 12 body in the form of a hole, such that the cage 12 is predominantly an annular (i.e., ring) configuration. The outer wall 20 preferably has a thickness T of from about 2.5 mm to about 5 mm, more preferably from about 3 mm to about 5 mm, and even more preferably about 3.5 mm. In some embodiments, the outer wall 20 comprises one or more lateral fenestrations that extend through the wall 20 from the exterior surface 22 to the interior surface 24 (not shown). When present, such fenestrations will permit bone growth not just in the vertical (i.e., proximal-to-distal) direction, but also horizontally (or laterally) out from the implant 10, providing additional rotational stability to the implant 10.

Figure 3:
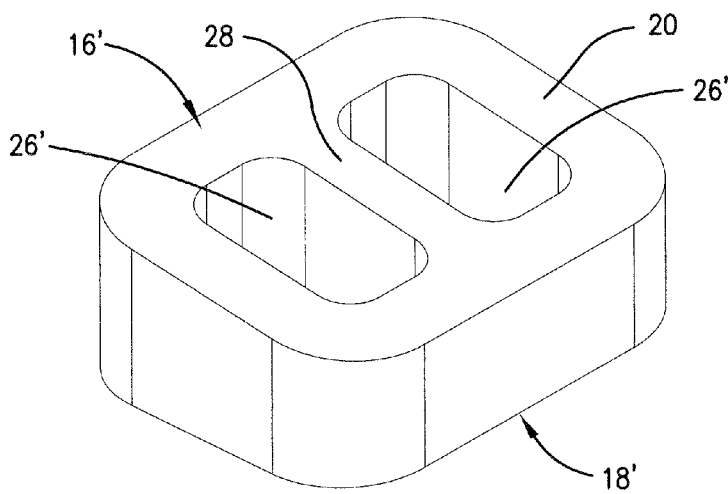
FIG. 3 is an isometric view of the implant cage in an alternative embodiment of the invention.
Figure 5:
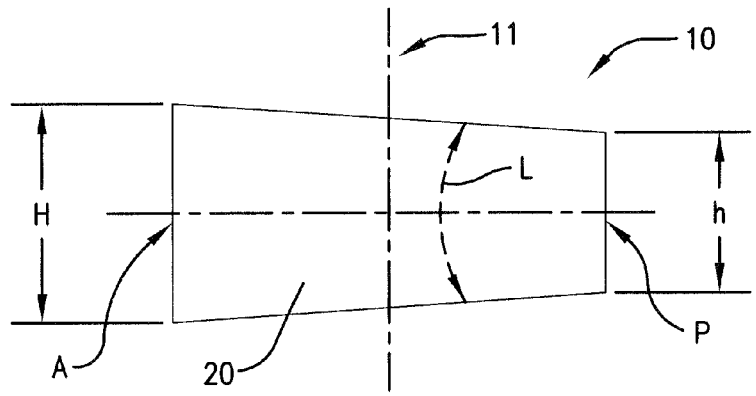
FIG. 5 is a side elevation view of an intervertebral implant in accordance with one or more embodiments of the invention.

As shown in FIG. 5, the cage 12, and correspondingly, the implant 10 includes an anterior face or portion A and a posterior face or portion P on either side of a bisecting plane 11 that extends in the generally vertical direction when viewing the implant 10 in a side profile view (i.e., the plane splits the implant generally in half from front to back). The anterior face or portion A corresponds to the anterior side of a patient when the implant 10 is inserted into the interbody space of the spine. Likewise, the posterior face or portion P of the implant 10 corresponds to the posterior side of the patient. In one or more embodiments, the cage 12 can further include one or more intermediate walls or struts 28 that subdivide the inner space 26 into more than one space or chamber 26', as shown in FIG. 3. When present, the intermediate wall 28 may extend between the superior surface 16 and inferior surface 18 of the cage 12 such that the intermediate wall 28 has respective superior 16' and inferior 18' surfaces, which are flush with the superior surface 16 and inferior surface 18 of the cage 12. Alternatively, the intermediate wall 28, may not extend the full height of the cage 12, such that the superior 16' and inferior 18' surfaces are offset or recessed from the respective planes defined by the superior surface 16 and inferior surface 18 of the cage 12 (not shown). The intermediate wall 28, when present, preferably extends in a direction generally from the anterior to posterior (i.e., in the front-to-back orientation), dividing the inner space 26 into right and left spaces 26' when implanted. In an alternative embodiment, the intermediate wall 28 may extend in a generally lateral direction (i.e., in the left-right orientation) dividing the inner space into front and back spaces when implanted (not shown).

With reference again to FIG. 1, the cage inner space 26 is preferably configured to receive the porous core 14 therein. The porous core 14 preferably fills at least a portion of the inner space(s) 26 of the cage 12. More preferably, the core 14 extends between opposed interior surfaces 24 of the cage 12, so that the core 14 is adjacent to and in contact with the interior surfaces 24 of the cage 12. In other words, there are preferably no gaps between the core 14 and the cage 12, with the shape and size of the inner space 26 corresponding to the shape and size of the core 14. The core 14 can be maintained in place in the cage 12 by any suitable method, including bonding the core 14 to the cage sidewalls using an adhesive, mechanical (e.g., friction fit) engagement of the core 14 and the cage 12, and/or molding the cage 12 over the core 14. The porous core 14 is preferably a self-sustaining body which serves as a scaffold for new bone tissue growth. The term "self-sustaining," as used herein means the body is substantially rigid and maintains its shape without an external support structure, and is not susceptible to deformation merely due to its own internal forces. In other words, although the core 14 is contained in the inner space 26 of the cage 12, the core 12 does not rely on the cage 14 for support or maintenance of shape. The porous core 14 body has a superior surface region 30 and an inferior surface region 32. In one or more embodiments, the superior surface region 30 of the core 14 is substantially flush with a plane defined by the superior surface 16 of the cage 12, such that the implant 10 presents a substantially uniform superior face for contacting/interfacing with an adjacent vertebral body 40. Likewise, in one or more embodiments, the inferior surface region 32 of the core is substantially flush with a plane defined by the inferior surface 18 of the cage 12, such that the implant 10 presents a substantially uniform inferior face for contacting/interfacing with an adjacent vertebral body 40. That is, the core 14 preferably does not extend past the plane defined by the respective superior 16 and inferior 18 surfaces of the cage 12, such that the inferior surface region 32 and inferior surface 18 cooperatively form the inferior face of the implant 10, while the superior surface region 30 and superior surface 16 cooperatively form the superior face of the implant 10.

Figure 4:
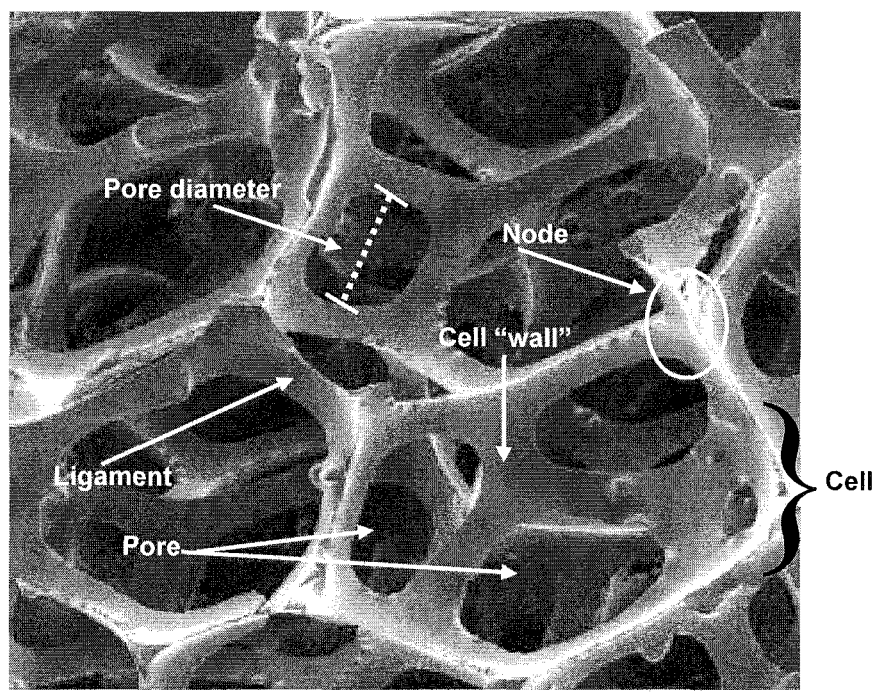
FIG. 4 is a scanning electron microscope (SEM) image of reticulated vitreous carbon (RVC) foam annotated to illustrate nodes, ligaments, and cells that make up the matrix microstructure.

The porous core 14 comprises a carbonaceous matrix characterized by a continuous phase having a surface and defining a plurality of open spaces (i.e., cavities, voids, and pores) throughout the matrix (i.e., internal and external open spaces). The continuous phase is formed of a carbonaceous material, and preferably consists essentially or even consists of the carbonaceous material. In one or more embodiments, the carbonaceous material is selected from the group consisting of carbon foam, graphite foam, and combinations thereof. Carbon and graphite foams are generally characterized by a three-dimensional bonding between carbon atoms ("nodes") to form cells, which are further interconnected via ligaments. The cell walls, nodes, and ligaments together create the interconnected network (i.e., continuous phase) of the matrix, which defines the open spaces of the matrix, with the pores being those open spaces or holes formed through the cell walls. Suitable carbon foams for use in the invention include, without limitation, pyrolytic carbon foams, vitreous carbon foams, and the like. For ease of reference, unless otherwise specified, the term "carbon foam" is used herein to include graphitic foams, although true (amorphous) carbon foams are particularly preferred for use in the invention. The carbonaceous matrix has an open cell structure, and more preferably is a reticulated carbon foam. FIG. 4 is an annotated SEM image of a reticulated carbon foam. Reticulated carbon foams have interconnected pores throughout the matrix which allow the passage of gas or fluid through the open spaces from one cell to the next, as opposed to closed cell structures in which the cells are totally enclosed by their walls and do not have interconnected openings. It will be appreciated that a combination of open and closed cell structures could also be present in the matrix; however, the matrix preferably primarily comprises an open cell structure. In other words, open cell matrices suitable for use in the invention may contain a small fraction of closed cells without departing from the intent of the invention.

Preferably the carbonaceous matrix has an average (median) pore diameter of at least about 50 μm, more preferably from about 80 to about 400 μm, and even more preferably from about from about 150 to about 250 μm. Pore diameter can be measured using micrograph images of the matrix, according to known standards in the art, as illustrated in FIG. 4. The matrix preferably has a porosity factor of at least about 80%, more preferably from about 75 to about 95%, and even more preferably from about 80 to about 90%. Porosity is the percentage of the volume of open or void space in the matrix as compared to the bulk volume of the matrix. It can be determined using fluid passage (or CT) techniques known in the art. The matrix preferably has a pore density (pores per linear inch or "PPI") of at least about 50, more preferably from about 75 to about 100, and even more preferably from about 80 to about 100, with about 80 being particularly preferred. Exemplary carbon foams for use in the invention are commercially available from various manufacturers, including, without limitation, ERG Aerospace Corp., Oakland, Calif. (DUOCEL® RVC 45, 60, 80, and 100 vitreous carbon foam); GrafTech International, Parma, Ohio (GRAFOAM® FPA-02, -05, -10, -20, and -35 graphitic foam); PocoGraphite, Inc., Decatur, Tex. (POCOfoam® graphitic foam); Koppers, Pittsburgh, Pa. (KFOAM® L1, L1a, and D1 graphitic foam); Touchstone Research Laboratory, Ltd., Triadelphia, W.V. (CFOAM® 20, or 25); and Ultramet, Pacoima Calif.

(RVC 65 PPI, 80 PPI, RVC with CVD materials, and RVC with integrally bonded coating). Methods for making carbon foams are also known in the art, including U.S. Pat. Nos. 6,103,149, 6,656,238, 6,656.239, and 6,749,652, incorporated by reference herein to the extent not inconsistent with the present disclosure.

The carbonaceous matrix is preferably substantially of a uniform material throughout its three-dimensional structure. That is, the core 14 preferably does not include any metals, plastics, composites, cements, or other inorganic structures or supports in, on, or through the body. As mentioned above, the matrix has self-supporting rigidity, with minimal bending, flexing, or compressing. The porous core 14 itself preferably has an ultimate stress capability of at least about 0.2 MPa, more preferably from about 1 to about 15 MPa, even more preferably from about 2 to about 15 MPa, and most preferably from about 10 to about 15 MPa.

The porous core 14 preferably further comprises a coating adjacent the continuous phase surface of the matrix. When present, at least about 75% of the continuous phase surface is preferably covered by the coating, more preferably at least about 85%, and even more preferably from about 95% to about 100% of the continuous phase surface is covered by the coating, based upon the total available surface area taken as 100%. Thus, both the exterior and the interior of the continuous phase surface of the matrix is preferably substantially covered by the coating. Solids, liquids, or combinations thereof can be used to form the coating. Solid coatings can be applied using plasma deposition techniques. Liquids (including gels or other fluids) can be applied by immersing or dipping the matrix into the liquid, spraying the liquid onto the matrix, or puddling the liquid onto the matrix and allowing it to permeate through the matrix pores. The coating can then be dried. Solids can also be dissolved or dispersed in a solvent system (e.g., distilled water) and applied as a liquid described above. Vacuum techniques can be used in conjunction with any of the above application methods to drive the coating material into the matrix. In any case, the matrix is "infused" with the coating material, such that the material is present as a coating, film, or monomolecular layer immobilized on and adjacent to the continuous surfaces throughout the interior and exterior of the matrix, but does not occlude the internal and/or external pores of the matrix. That is, after coating, less than about 10% of the pores are occluded by the coating material, preferably less than about 5%, and more preferably less than about 1% of the pores are occluded by the coating material. It will be appreciated that certain coating materials may have a tendency to occlude the pores of the matrix, or may be of a sufficient thickness as to significantly narrow the pore size; thus, it may be desirable to select a matrix having a higher initial porosity, or larger average pore diameter, such that the porosity or average pore diameter after coating remains within the target values disclosed herein.

Suitable coating materials are selected from the group consisting of osteopromotive agents, therapeutic agents, and combinations thereof. "Osteopromotive" agents are materials that facilitate or enhance bone formation. It will be appreciated that a given coating material can be both osteopromotive and therapeutic, and these categories are descriptive and not necessarily mutually exclusive. Osteopromotive materials include both osteoinductive compositions and osteoconductive compositions. By comparison, osteoconductive compositions are ones which permit and even enhance bone growth over the surface of the material, and include allogenic or autogenic bone fragments, calcium phosphate, hydroxyapatite, coralline, sintered bone (Bio Oss®), porous polycaprolactone, and combinations thereof. Osteoinduction involves in-growth of bone tissue into (and not just over) the material.

Other suitable osteopromotive agents for use in the invention include naturally-occurring cytokines and growth factors found principally in bone but in other tissues as well. Exemplary osteopromotive agents include bone morphogenetic proteins (BMP, isoforms 2, 4 and 7), transforming growth factors beta-I and beta-II, fibroblastic growth factors, angiopoietin 1, vascular endothelial growth factor, platelet-derived growth factor, parathyroid hormone and insulin-like growth factors. These materials can be coated onto and delivered, for example, using the osteoconductive materials identified herein, as either biochemical preparations obtained from human or animal tissues, or preferably, as highly-purified single proteins produced via recombinant DNA expression technologies. Other osteopromotive agents suitable for use in the invention include nucleic acid vectors (e.g., plasmid DNA, cDNA, adenovirus-associated or RNAi constructs) known to be osteopromotive from in vitro or preclinical studies.

Therapeutic agents for use in the invention include small molecule drugs as well as biologics. Exemplary small molecule drugs include antibiotics (e.g., vancomycin, tobramycin, gentamicin, nanoparticulate silver), anti-inflammatories (e.g., COX-1, COX-2, steroidals), and anti-coagulants (e.g., conjugated heparins, warfarin). Exemplary therapeutic biologics include proteins isolated from animal tissues such as collagen, albumin, fibrin, fibrinogen, vitronectin, and immunoglobulins, as well as synthetic, therapeutic monoclonal antibodies.

It will be appreciated that many of the above materials may be used alone or in combination in the coating. It will also be appreciated that the above materials can be combined with osteogenic bone-forming strategies involving the ex vivo manipulation, material adhesion, replication and differentiated function of exogenous cells to the osteoconductive materials discussed above. For example, explanted, minimally-manipulated cells from either the patient (autograft) or donors (allograft) can be used to enhance bone growth, including adult stem cells (e.g., bone marrow, adipose, umbilical cord blood, etc.), bone-derived osteoblasts, chondrocytes isolated from cartilage, and complex, undefined cell populations current in clinical use, including bone marrow aspirate and platelet-rich plasma. Genetically manipulated allogeneic, immunocompatible cells expressing osteoinductive growth factors, cytokines or cell attachment proteins may also have therapeutic potential in the context of the materials described herein.

In one or more embodiments, the coating is immobilized on the continuous phase surface of the carbonaceous matrix, but preferably is not covalently or otherwise chemically bonded thereto. Thus, the coating material is physically immobilized, relying instead on van der Waals or ionic-type attraction between the carbonaceous matrix continuous phase surface and the coating material. This provides a significant advantage in that the osteopromotive or therapeutic agents do not have to be chemically modified, and thus retain their full bioavailability when implanted into a patient, even though tightly bound to the matrix. Advantageously, the use of the coating in combination with the carbonaceous matrix permits not just in-growth of bone, but eventual through-growth of bone throughout the entirety of the matrix, as discussed in more detail below. The carbonaceous matrix is characterized by the ability to retain proteins loaded onto the matrix. More specifically, the porous body, when subjected to a protein elution test, as described herein, has the ability to retain at least about 30% of protein, more preferably at least about 40% of protein, and even more preferably at least about 50% of protein during formation of the coating. That is, when the matrix is infused with a solution containing a protein, such as BMP, at least about 30% of the protein from the free solution will be taken up and retained by the matrix (preferably at least about 40% and more preferably at least about 50%), based upon the total amount of protein in the solution taken as 100%. In other words, the protein content of the solution is decreased by at least about 30, 40, or preferably 50% after immersing the matrix into and then removing it from the solution.

Protein retention can be tested using a protein elution test as described herein. A important aspect of the invention is the integration of biologically active cytokines or other biological materials within the carbon foam matrix (present as coatings of the material). The protein elution tests of this application are multi-partite and address important functional issues of productive contact between osteoinductive material and conductive carbon foam matrices, the degree of persistence of the binding interaction, the percentage of coating released to the surrounding milieu, and percentage retained in a biologically-active, bio-available form. An example of one such comprehensive analysis involves contacting selected foam materials with a cytokine solution of known concentration either by passage of the solution over the solid object or by low pressure vacuum loading. The concentration of the remaining wash solution following completion of a specified loading time is reevaluated by ELISA to determine the cytokine depletion and thus de facto transfer of cytokine to the carbon foam. Replicate loading studies using recombinant human BMP-2 (rhBMP) reliably yield depletion values of 50%, that is, simple contact between solute and carbon material yields transfer of 50% of the cytokine to the carbon foam from solution. Verification of this presumptive loading percentage can be validated using one of two methods: 1) Liquid phase ELISA of protein stripped from coated carbon foams with chaotropic agents (e.g., 4M guanidine hydrochloride) or reagents that interfere with ionic interaction (e.g., 5M NaCl; 0.5M glycine, NaOH, pH 10); or 2) Solid-phase ELISA of cytokine adsorbed to carbon matrix using BMP-2 antibody conjugated to biotin or chromogenic-generating enzyme providing quantification of the amount of BMP-2 adsorbed onto the material surface.

Bound BMPs (such as BMP-2 or other cytokines described herein) can also be evaluated by the criterion of biological activity by exposure of responding cells lines that are competent to respond to the adsorbed cytokine in question. That is, cells exposed to cytokine-coated matrices can readily be induced to develop novel phenotypes such as a bone-forming osteoblast that can be measured using a combination of enzymatic, molecular (real time PCR), and histochemical assays. This is important for retention of biological activity (rather than migration away from) at the clinically-relevant site of implantation.

In addition, the matrix has a remarkable ability to retain the coating in the matrix after implantation, drawing the components of the bone regeneration process into the matrix. This is particularly advantageous for the use of proteins such as BMP, which are retained by the matrix instead of being released into surrounding tissue, and avoids the formation of ectopic bone or unwanted bone overgrowth. After implantation, the porous body will preferably retain at least about 75%, more preferably at least about 80%, even more preferably at least about 90%, and most preferably at least about 95% of the immobilized protein, based upon the total initial protein content of the coating taken as 100%. This can be tested in vitro for a given matrix prior to implantation using a protein release test, as described in the working examples.

Thus, when subjected to a protein release test for a period of about a week, implants according to the invention will have high retention and low release of bound protein. Thus, the rate of mineralization can be reliably controlled using the inventive implant, due to the linear relationship between the amount of osteopromotive material (such as BMP) present in the implant, and the mineralization rate. Accordingly, a given amount of protein can be loaded onto the matrix before implantation to achieve a target level of mineralization, since very little protein is lost to surrounding tissue.

In one or more embodiments, the porous core consists essentially or even consists of the carbonaceous matrix and coating. That is, the porous core is substantially free of metals (such as titanium, titanium alloys, steel, tantalum, copper, silver, or cobalt chromium alloy), composites, plastics and polymers (such as polypropylene, polymethylmethacrylate, polyethylene, polyoxymethylene), and the like. The term "substantially free," as used herein, means that the porous core comprises less than about 1% by weight of a given substance, more preferably less than about 0.1% by weight of a given substance, and even more preferably about 0% by weight of a given substance, based upon the total weight of the core taken as 100% by weight.

Figures 6A, 6B:
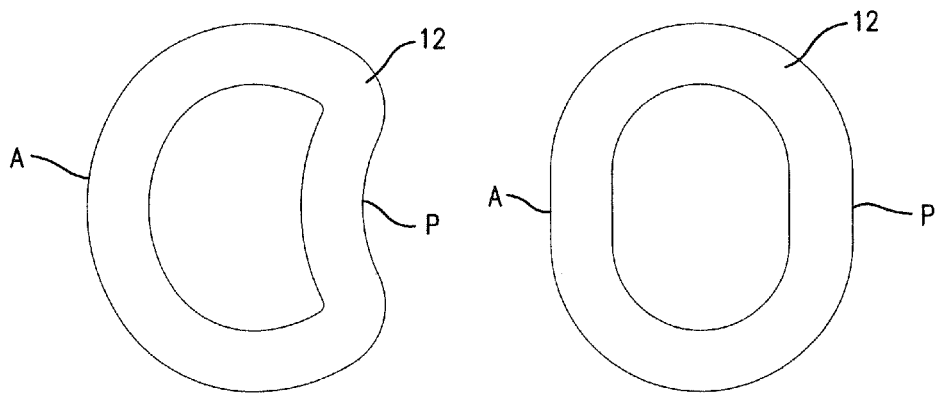
FIG. 6a-e show a top-down view of various implant shapes in accordance with one or more embodiments of the invention.
Figures 6C, 6D:
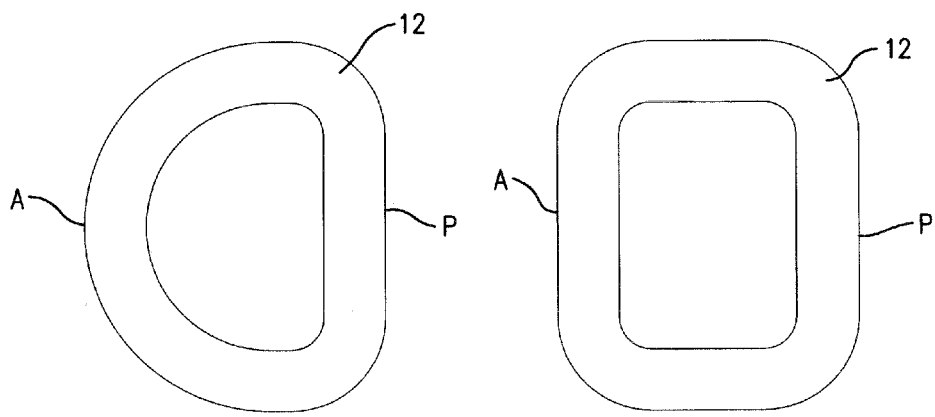
Figure 6E:
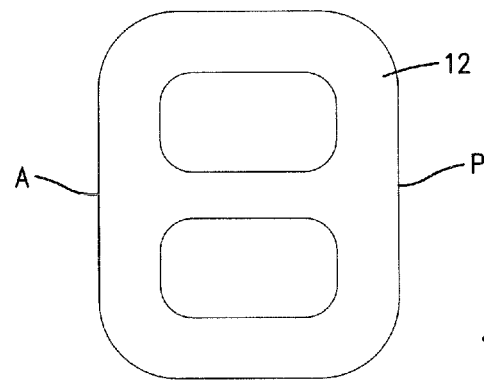
Figure 10:
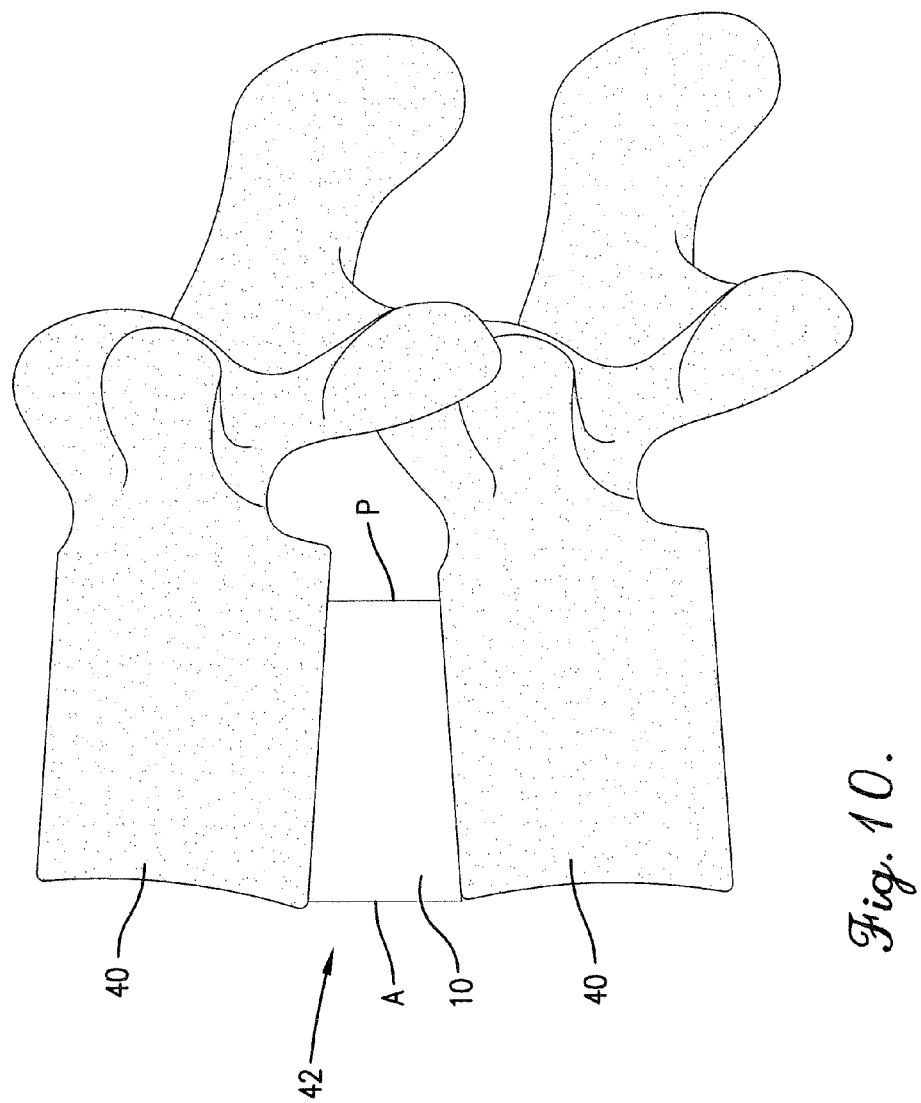
FIG. 10 is a side elevation view of the intervertebral implant inserted between adjacent vertebral bodies.

Referring again to FIG. 5, in one or more embodiments, the implant 10 has a wedge profile, to restore not only anatomical height, but also anatomical lordosis to the spine when inserted. Thus, the height H of the anterior face or portion A of the implant 10 is preferably greater than the height h of the posterior face or portion P of the implant 10. Thus, the height of the implant 10 gradually decreases (or tapers) from the anterior portion A to the posterior portion P. It will be appreciated that the angle of the wedge (L) will vary depending upon the intended location in the spine. In addition, the size of the implant will vary depending upon the size of the patient. More specifically, the lordotic angle L of the implant will preferably range from about 4° to about 14°, based upon posterior implant heights h ranging from about 8 to about 22 mm for lumbar implants and from about 5 to about 12 mm for cervical implants. Likewise, the anatomical footprint of the cage (i.e., width, depth, and shape) will also vary depending upon the intended location in the spine, as well as the size of the patient. It will be appreciated that the shape of the implant can vary widely, although the maximum width dimension of a given shape will typically be from about 15 mm to about 35 mm, and more preferably from about 20 mm to about 30 mm. The maximum depth dimension of a given shape will typically range from about 15 mm to about 30 mm, and more preferably from about 20 mm to about 25 mm. In some cases, the implant can be of a symmetrical shape, such that the anterior portion A is a mirror image of the posterior portion P when viewed from the top-down, such as the in case of a circular cage. In other cases, the anterior portion A or posterior portion P may be flattened, bent or curved to produce the desired shape. Various possible shapes are shown in FIG. 6, from kidney bean shaped, oval, circular, square, ellipsoid, horseshoe, D-shaped, etc. Preferably, the implant 10 is provided in a shape configured for maximum surface-to-surface contact/interfacing with the endplates of adjacent vertebral bodies 40, as shown in FIG. 10. Thus, in preferred embodiments, the implant 10 shape mimics the anatomical footprint of the disc or portion being replaced.

Figure 7:
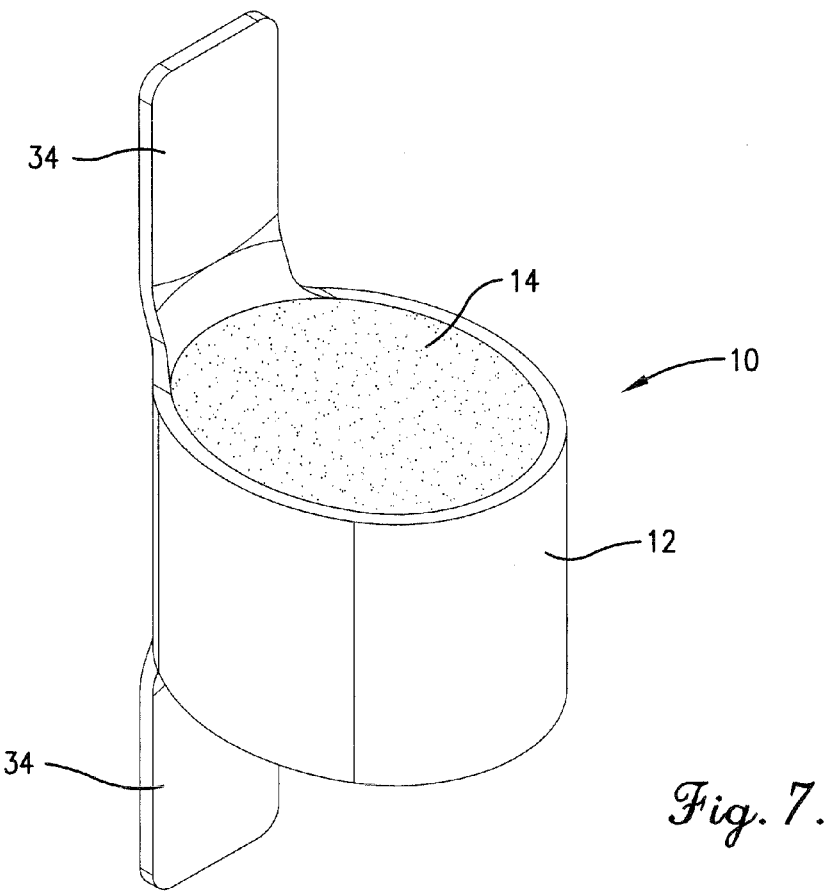
FIG. 7 is an isometric view of an intervertebral implant configured for implantation in the cervical region of the spine in accordance with one or more embodiments of the invention.

For implantation in the cervical region of the spine, the implant 10 is preferably provided with wings 34 for fixation of the device to the vertebral column. This embodiment is depicted in FIG. 7, and includes the cage 12 and porous core 14 as described above.

Figure 8:
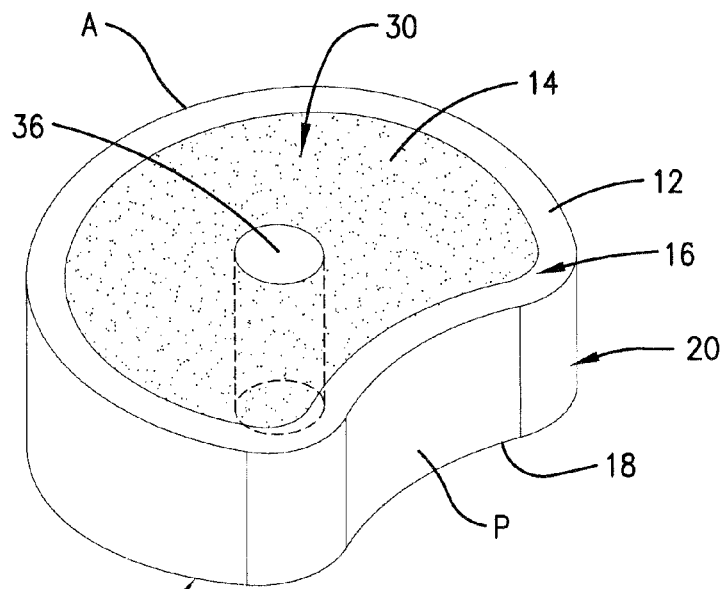
FIG. 8 is an isometric view of an intervertebral implant having an axial hole through the porous core for packing bone graft material in accordance with one or more alternative embodiments of the invention.
Figure 9:
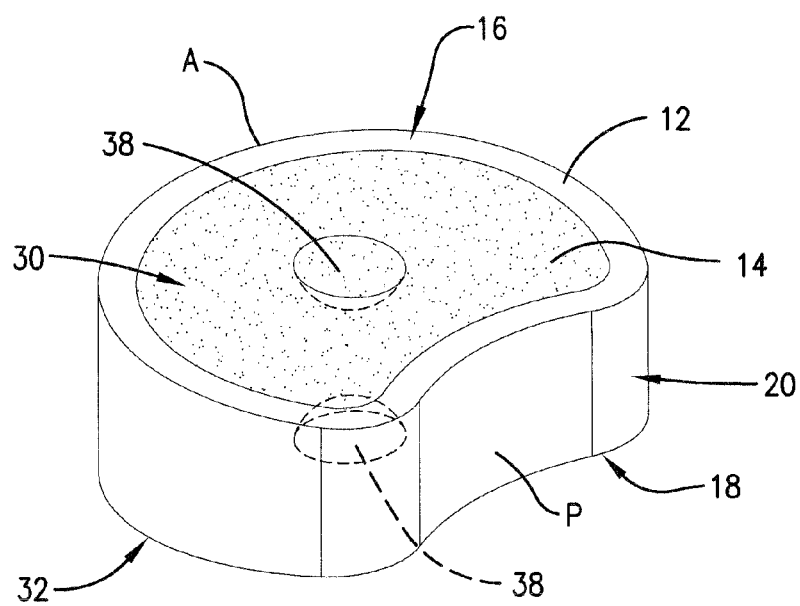
FIG. 9 is an isometric view of an intervertebral implant having a divot in the porous core for packing bone graft material in accordance with one or more alternative embodiments of the invention.

In use, the surgeon will excise the dysfunctional intervertebral disc from the patient. The explanted tissue can be used to generate morselized autograft. Alternatively, another tissue can be used for the autograft (e.g., iliac crest), or an allograft, or xenograft material can be used. A significant advantage of the inventive implant is that the porous core 14 can be readily shaped on-site by the surgeon or other technician. In other words, the porous core can be shaped immediately prior to packing with bone grafting material and implanting the implant into the subject (preferably less than about 90 minutes prior to implantation, more preferably less than about 60 minutes, and even more preferably less than about 30 minutes prior to implantation). Shaping can be carried out using conventional surgical tools, such as scalpels, bone saws, drills, or Dremel®-type tools (e.g., grinders) to provide one or more axial canals 36 (i.e., through holes) as shown in FIG. 8, or depressions 38, as shown in FIG. 9, for packing morselized bone, if a grafting material is to be used for the procedure. The surgeon can modify the core 14 for the precise amount of grafting material to be used, which is then packed in the hole(s) or depression(s). In one or more embodiments, the implant 10 can be provided pre-shaped with a hole or depression for packing the grafting material. The hole or depression can be further modified, if necessary, or used as-is. In another embodiment, the implant 10 can be provided with a drill kit containing drills or bits marked for different volumes of bone grafting material. The volume of the available bone grafting material to be used will be measured by the surgeon. The surgeon will then select the appropriate drill or bit corresponding to this volume, and then drill the precise-sized void into the core for the available volume of bone grafting material. Typically only one hole or depression will be made, and may be formed on the superior side, the inferior side, or both sides of the core. It will be appreciated that although the figures depict these holes or depression as being centered on the implant, the placement of the hole or depression may be off-center. The customized hole or depression will then be packed with the grafting material.

In a further embodiment, the surgeon may decide against using a graft, in which case, the core 14 is not modified or bored through. The customizability of the inventive implants saves the surgeon from having to pack the hole traditionally provided in conventional implants with another type of biocompatible material to avoid leaving a void space in the implant.

The intervertebral implant 10 is then placed into the interbody disc space 42 to restore the original disc height and lordosis, as shown in FIG. 10 for a lumbar implant. The inventive implant can be inserted using any conventional surgical techniques, and is suitable for anterior, anterolateral, lateral, and/or posterior methods (including anterior lumbar interbody fusion (ALIF) and posterior lumbar interbody fusion (PLIF)). The implant does not require any special insertion tools. In some embodiments, surface roughness 19 (e.g., teeth) can help prevent the implant 10 from being expelled from the interbody space. The implant 10 can be further secured using a supplemental fixation system, such as screws, rods, plates, or any combination thereof.

Once implanted, the cage 12 provides resistance to compressive and rotational forces encountered by the spine to maintain the required disc space and lordotic angle, as well as resist subsidence. In particular, the implant 10 will preferably withstand about 200% of the load to failure associated with the human vertebral body and vertebral disc. For a lumbar spinal implant, the compressive loading of the implant 10 will preferably exceed 16,000 N. The compressive loading is measured by ASTM F2077-11 (Test Methods For Intervertebral Body Fusion Devices).

Figure 11:
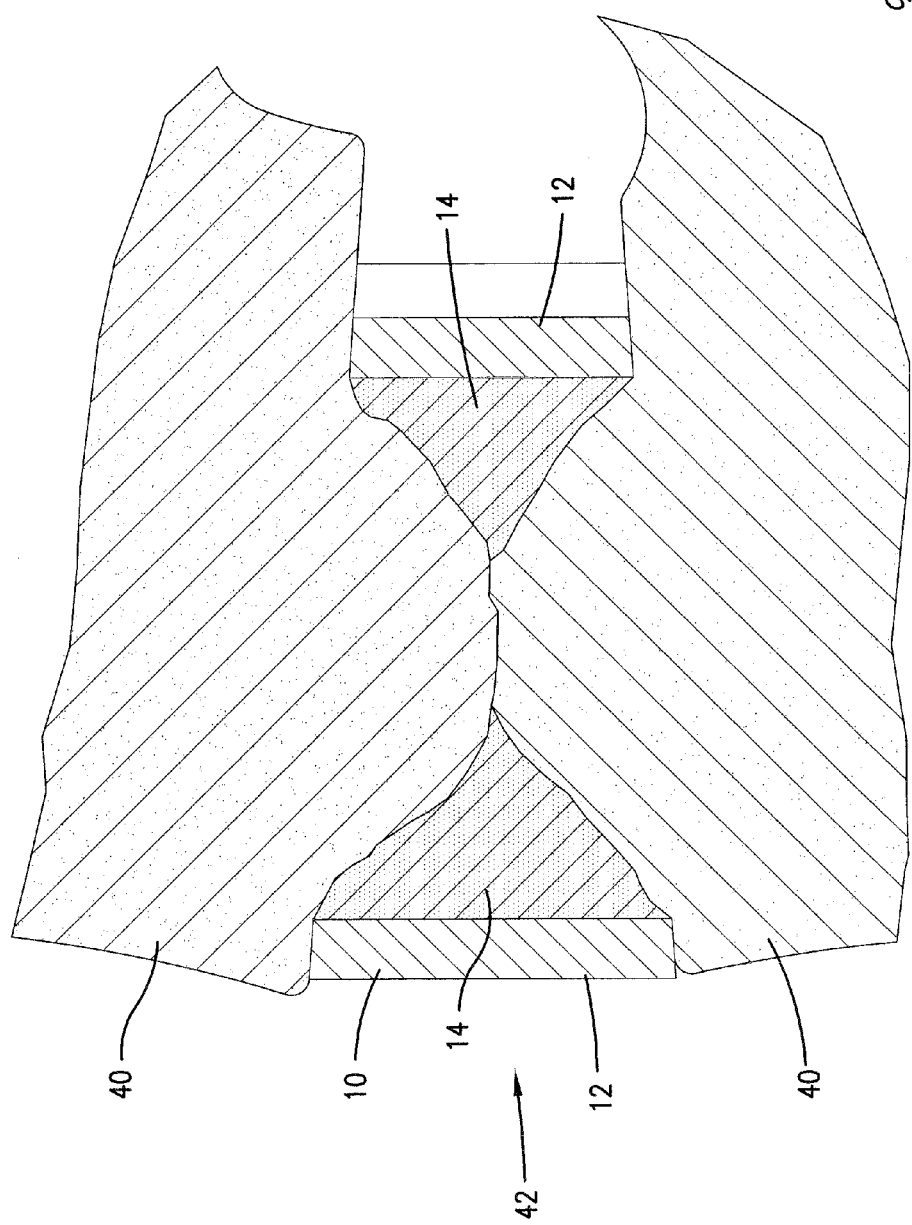
FIG. 11 is cross-sectional side elevation of the bony through-growth through the porous core of the implant in accordance with one or more embodiments of the invention.

Once implanted, osteogenesis begins, which involves bone and tissue ingrowth into the porous core, including the establishment and maintenance of a vascular bed in the matrix, eventually resulting in new bone formation (mineralization). Unlike many existing implants, the patient's vascular supply is able to readily penetrate through the porous core 14 of the implant 10, which supports the development of new blood vessels that are essential to bone growth and allows the formation of a robust vascular bed. Advantageously, the inventive implant 10 supports vascularization throughout the entirety of the matrix, resulting in not just in-growth of bone tissue at the vertebral body 40/implant 10 interface, but "through-growth" of bone tissue through the entire matrix body, as shown in FIG. 11, fusing the adjacent vertebral bodies 40 not just to the implant 10, but ultimately to each other. In particular, proximal to distal bone growth from adjacent vertebral bodies 40, which remains aligned with the original implant position, can be observed. As bone tissue infiltrates the matrix and mineralizes, the porous body of the core is slowly degraded and resorbed by the patient's body. More preferably, at about 6 weeks after implantation, the porous core is preferably at least about 75% resorbed, more preferably at least about 85% resorbed, and even more preferably at least about 95% resorbed. In other words, at about 6 weeks after implantation, the replaced disc area will comprise less than about 25% carbonaceous material from the porous core, more preferably less than about 15% carbonaceous material, and even more preferably less than about 5% carbonaceous material, based upon the total initial carbon content of the porous core taken as 100%. The terms "resorption" and "bioresorption" are used interchangeably herein and mean that the material is broken down and absorbed by the body over time and does not require mechanical removal from the body. A particularly unexpected aspect of the invention is that direct displacement/replacement of the porous core by the new tissue will preferably be observed, as opposed to overgrowth of tissue. This through-growth of bone in alignment with the original implant position is a surprising and particularly advantageous aspect of the present invention.

The volume of the cage 12 itself is not replaced or bioresorbed, but remains a permanent fixture in the patient, unless removed. However, the risk of subsidence into adjacent vertebral bodies is low because of the complete bony fusion achieved through the bioresorption of the core, which permits a higher volume of bone fusion between adjacent vertebral bodies in the proximal to distal direction through the cage 12. This new bony column ultimately becomes the weight-bearing structure long-term, as opposed to the cage 12.

The invention described herein is discussed primarily with respect human-based therapies; however, it will be appreciated that the treatment can be applied for clinical research or therapeutic treatment to any suitable animal, including, without limitation, dogs, cats, and other pets, as well as, rodents, primates, horses, cattle, etc. Additional advantages of the invention will be apparent to those skilled in the art upon review of the disclosure herein and the working examples below.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone;

B alone; C alone; A and B in combination; A and C in combination; B and C in combination; or A, B, and C combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Certain terminology is used herein for convenience only and is not limiting. For example, the words "right," "left," "superior," "inferior," "vertical," and other directional terms designate directions in the drawings to which reference is made.

EXAMPLES

The following examples set forth methods in accordance with the invention. It is to be understood, however, that these examples are provided by way of illustration and nothing therein should be taken as a limitation upon the overall scope of the invention.

Example 1

Osteoinductive Properties of Vitreous Carbon Foam Materials

1. Materials and Methods

In this Example, 6×5 mm carbon foam discs (DUOCEL®, ERG Aerospace) prepared from bulk materials were sterilized in 70% ethanol and exhaustively rinsed in phosphate buffered saline (PBS). For BMP-2 loading studies, foam discs were submerged in PBS containing specified amounts of cytokine for 24 hours. Unbound cytokine was separated from the foam-bound fraction by low-speed centrifugation, followed by 3 rinses in PBS. The BMP-2 that was not adsorbed by the carbon foam was measured in the residual soak and subsequent wash solutions using a sandwich ELISA assay.

The rinsed discs containing adsorbed BMP-2 were then placed into wells of a tissue culture plate and C2C12 mouse myoblast cells were added to the carbon matrix by direct pipetting. Carbon materials pre-incubated in PBS containing 50, 100 or 200 ng/ml BMP-2 comprised the experimental study groups. Cell culture medium was added to the plates containing the cells and carbon matrix following a 2 hr attachment. Negative control C2C12 cell cultures received no additional material while positive controls received soluble BMP-2 applied to cells already adhered to tissue culture polystyrene. Four days later, rinsed cell monolayers or three dimensional cultures on carbon foam were lysed and alkaline phosphatase activities determined in the cell extracts. Alkaline phosphatase specific activities were determined by normalization against cell numbers in parallel cultures using an MTT cell viability assay.

The intrinsic osteoinductivity of DUOCEL® carbon foam was evaluated by material infiltration of C2C12 mouse myoblasts or NHOSC human osteoblasts into rinsed carbon foam discs followed by measurement of alkaline phosphatase induction. Control cell cultures were 2-dimensional cell monolayers on tissue culture polystyrene. Enzyme specific activities were determined at 2, 4, and 6 days (C2C12) or at days 3, 5 and 7 days (NHOSC cells).

2. Results

Figure 12:
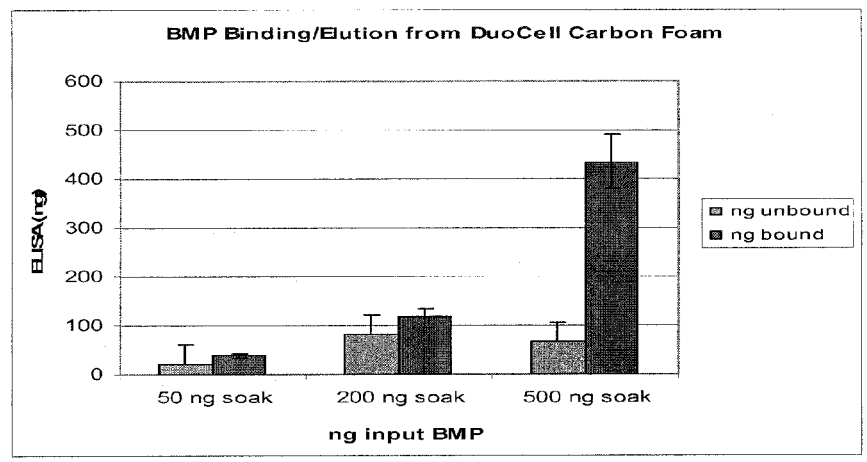
FIG. 12 is a graph of the results of the BMP-2 binding assays using carbon foam discs incubated 24 hr in solutions containing the indicated mass of cytokine from Example 1.

A typical outcome of a BMP-2 adsorption assay using DUOCEL® carbon foam is depicted in FIG. 12. Unbound values were derived by ELISA and bound values by subtraction of unbound from input. At lower BMP-2 inputs (50 and 100 ng/ml) the adsorbed and non-adsorbed fractions were approximately equal. At a higher BMP-2 input (500 ng/ml) the adsorbed:nonadsorbed ratio tended to increase from 1:1 to a value of circa 5:1. Aggregate results of several trials show BMP-2 concentration-dependence of binding at constant carbon foam mass input (data not shown).

Figure 13:
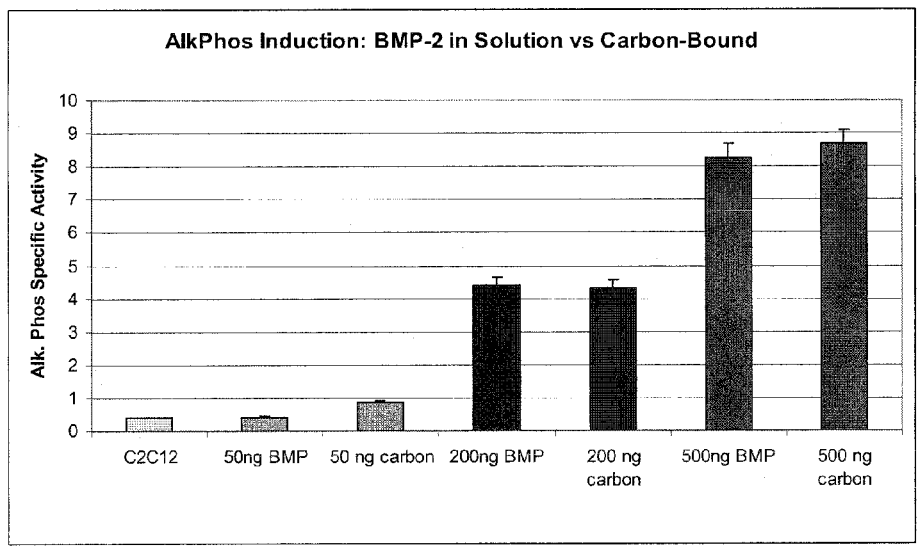
FIG. 13 is a graph of the results of the alkaline phosphatase induction in C2C12 myoblasts exposed to soluble BMP-2 and carbon foam discs pre-adsorbed in cytokine solutions of the same concentrations from Example 1.

To assess both the relative amount of BMP-2 bound to the carbon discs and whether biological activity is retained following adsorption, C2C12 myoblasts were exposed to rinsed discs and alkaline phosphatase activity was measure 4 days later (FIG. 13). This mouse myoblast cell line is capable of acquiring a bone cell (osteoblast) phenotype upon exposure to osteoinductive cytokines (including BMP-2) and thus provides a valid bioassay system for cytokine-provoked cell signaling. Alkaline phosphatase induction provides a reliable phenotypic marker of a commitment to the osteoblast phenotype in cells so provoked. Significantly, carbon foam discs pre-adsorbed in the indicated BMP-2 solutions induced an amount of alkaline phosphatase activity that was identical to positive control C2C12 cell culture receiving the same amount of soluble cytokine. This outcome indicates that the levels of alkaline phosphatase activity induced by treated carbon foam is the resultant of both adsorbed cytokine and intrinsic material osteoinductivity since the amount of BMP-2 retained by the discs was only approximately 50-80% of the original soak solution (FIG. 12).

Figure 14:
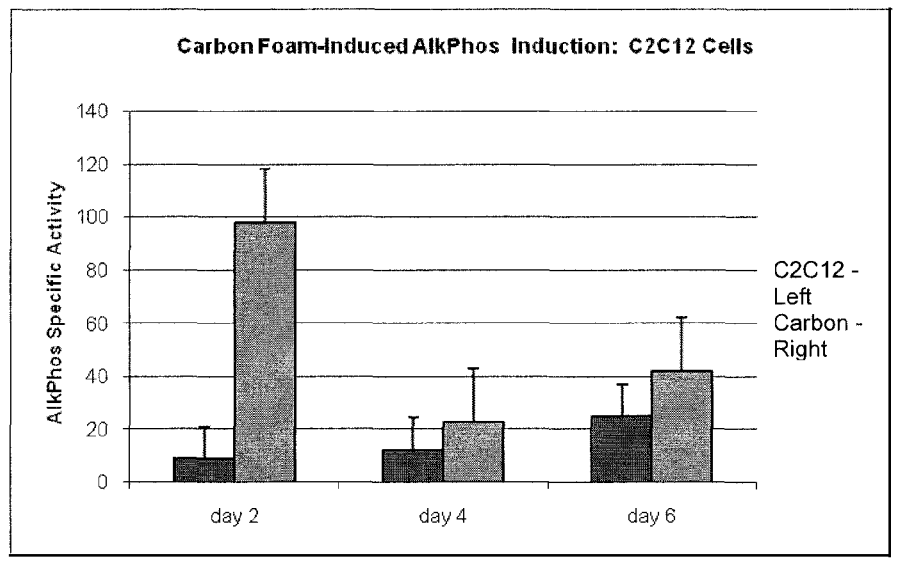
FIG. 14 is a graph of the results of the carbon foam induction of alkaline phosphatase activity in mouse C2C12 myoblast cells as compared with unchallenged controls from Example 1.
Figure 15:
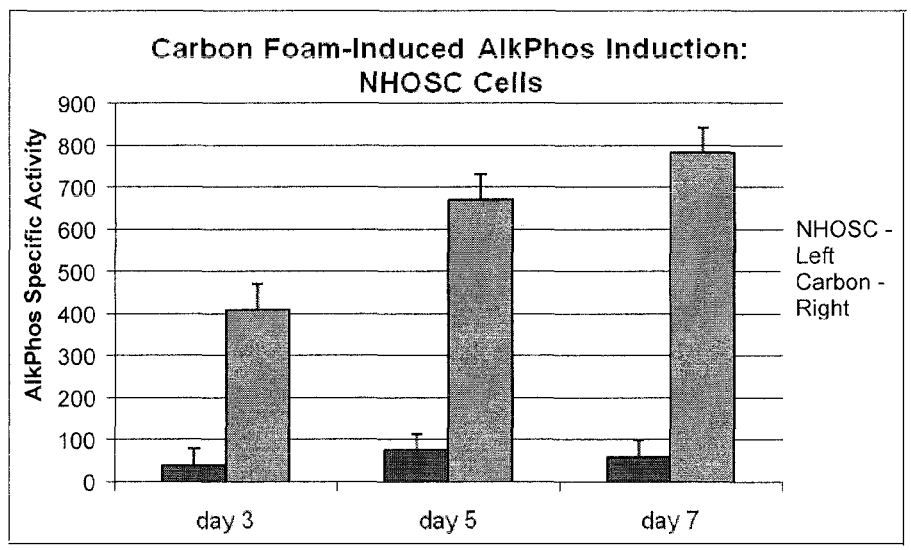
FIG. 15 is a graph of the results of the carbon foam induction of alkaline phosphatase activity in human NHOSC osteoblast cells as compared with unchallenged controls.

Alkaline phosphatase induction experiments (over a 6-7 day period) were also conducted using DUOCEL® carbon foam following exposure of mouse C2C12 myoblasts and human NHOSC osteoblasts (FIGS. 14 and 15). The former cell line addresses the ability of a predetermined cell type to re-differentiate and the latter the ability of an osteoblast to up-regulate a specific cellular phenotype. Both cell lines challenged with biomaterial exhibited increases in alkaline phosphates specific activity. The C2C12 cells trended towards higher activities than controls at all time points but was statistically significant from controls at day 2 only (FIG. 14). In contrast, the NHOSC cell line responded to carbon foam by synthesizing 8- to 10-fold higher levels of alkaline phosphatase that was statistically significant across the entire time interval (FIG. 15). Parallel analyses of enhanced osteoblast-like gene expression by RT-PCR have revealed similar trends (data not shown).

3. Conclusions

Carbon foam materials incorporate physical properties that mimic natural bone. Chief among these include mechanical rigidity, pore diameter, and pore interconnectivity, properties that contributed to the significant bone forming tendencies documented in the present studies. These tendencies include both the propensity of the materials to adsorb BMP-2 in a signaling-competent chemical form and the provision of a three-dimensional framework that allows bone cell (osteoblast) phenotypes to be expressed even in cells displaying a pre-determined phenotype. These two outcomes are consistent with the historical scientific literature pertaining to the topic of bone cell differentiation and concomitant predictors of materials and medical devices whose clinical outcomes culminate in significant bone formation. These results demonstrate the osteoinductive biomaterial property of carbon foam.

Example 2

Biomaterial Analysis for Mechanical Properties

Mechanical testing of a carbon foam material DUOCEL® with a pore size of about 120 μm was performed with strict adherence to the ASTM Standard Test Method for Compressive Properties of Rigid Plastics (ASTM D-695-02a). The material was machined into cylindrical-shaped specimens with a diameter of 1 cm and thickness of 2 cm. The specimens were then tested for mechanical properties using an MTS 858 Bionix material testing system (MTS Model 858, Eden Prairie, Minn.). Load and deflection data were measured and collected by the MTS system every 0.1 seconds. Each specimen was tested in compression loading from 0N to complete structural failure at a loading rate of 1.3 mm/min. The maximum stress was then determined, and the results are shown in the table below.

TABLE 1

Mechanical Properties of Carbon Foam

|  | Ultimate Load (N) | Ultimate Stress (MPa) | Ultimate Displacement (mm) | Ultimate Strain (MPa) |
|---|---|---|---|---|
| Average | 1693 | 12.57 | 0.94 | 0.026 |
| SD | 240 | 1.75 | 0.41 | 0.006 |
| Max | 2013 | 14.91 | 1.99 | 0.040 |
| Min | 1192 | 8.91 | 0.67 | 0.020 |

The significant parameter is "ultimate stress" which yielded a value of 12.57 MPa, a value equivalent to the ultimate stress capability of low-medium density trabecular bone. The data indicate that the carbon foam meets or exceeds the properties of human trabecular bone tested under similar conditions (10-50 MPa), indicating that carbon foam can achieve appropriate mechanical properties to serve as a bone void filler, even for weight-bearing applications.

Example 3

In Vitro Biocompatibility of Carbon Foam

1. Initial Testing

Figure 16:
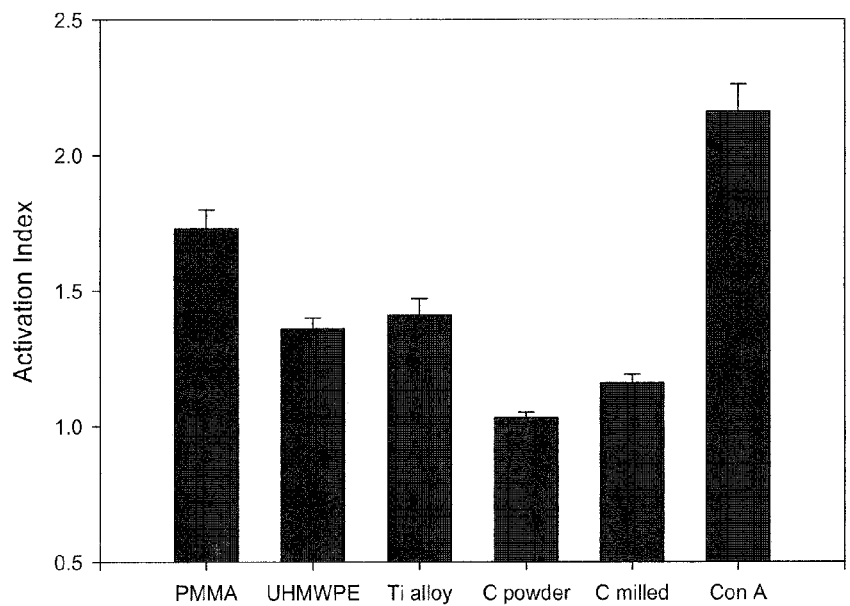
FIG. 16 is a graph of the activation indices for each material tested in Example 3.

Initial biocompatibility of carbon foam was conducted using a cell culture system developed in our laboratory for the evaluation of patient hypersensitivity to orthopedic biomaterials. Carbon in both powdered and milled fiber forms was evaluated using mononuclear cells (MNCs) obtained from 40 osteoarthritic patients under investigation for biomaterial sensitivity, along with other conventional biomaterials (polymethylmethacrylate (PMMA), Ti alloy, ultra-high-molecular-weight polyethylene (UHMWPE)). Peripheral blood was obtained from patients and MNCs were separated using Histopaque gradients. Cell suspensions of $2.5 \times 10^6$ cells were dispensed into wells containing various concentrations of biomaterial particles. Wells with no particles (negative control) or with Concanavalin A (ConA) (positive control) were also included on the plate. Plates were incubated for 6 days. Next, 20 μl of MTT solution (5 mg/ml) were then to each well, and incubation continued at 37° C. for 6 hours. The medium was then replaced by 10% sodium dodecyl sulphate (SDS), and the optical density (OD) of the resulting solution was read at 590 nm. Cell responses were then determined. Stimulation indexes (SI) for each response were calculated by comparison with background proliferation (medium control). The data (FIG. 16) indicate that carbon in either powder or milled fiber form provoked extremely low levels of cell activation when compared with other orthopedic biomaterials, and generated a significantly ($p<0.01$) lower response than PMMA, which is commonly used as a bone void filler during current orthopedic procedures. The data suggest that carbon implantation materials or degradation products do not pose an overt risk of either inflammatory reactions or tissue toxicity if used as bone void fillers.

2. Additional In Vitro Testing

Figure 17:
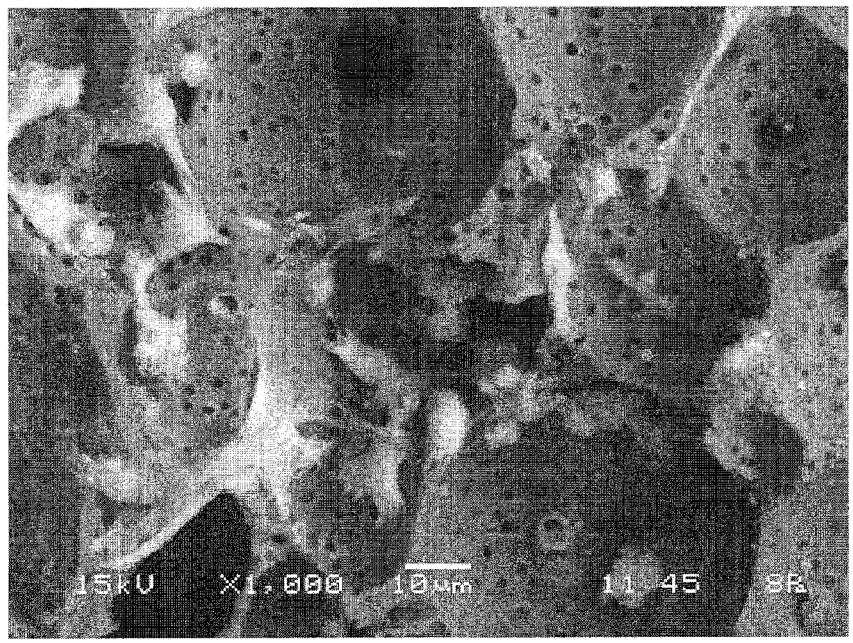
FIG. 17 is an SEM image of cellular attachment and colonization on a carbon foam scaffold from Example 3.

Further in vitro testing was conducted to evaluate cellular growth characteristics on carbon foam substrates using the RAW 264.7 mouse monocyte/macrophage cell line, and cells from rat bone marrow cultures induced to differentiate into osteoblasts in DMEM media supplemented with glycerol phosphate, L-ascorbic acid, and dexamethasone. Aliquots of 50 μl suspensions ($3.5 \times 10^6$ cells/ml) were loaded onto carbon foam scaffolds in 6-well plates and left undisturbed in a 37° C. incubator for 3 hours to allow cells to attach to the scaffold. At day 3, samples were harvested for morphological evaluation. Scaffolds with cultured cells were fixed with 1.5% glutaraldehyde (Fisher Scientific, US) for 30 min. at 4° C., and the samples were washed twice in PBS and then exposed to 2% osmium tetroxide (Sigma-Aldrich, US) for 30 min. The samples were then rinsed in distilled water, and dehydrated through a graded series of ethanol (50, 70, 90, and 100%) for 2-5 min., with and the dehydration completed in hexamethyl disilazane (HMDS) (Fluka, Germany) for 10 min. After air-drying, the samples were mounted onto SEM stubs and images were observed at 10 kV. Images were evaluated for cellular attachment and surface occupancy on the scaffolds. The results are shown in FIG. 17 and indicate that the RAW 264.7 cells had adhesion and colonization on the scaffold after three days in culture. Dye exclusion techniques also revealed a high level of viability.

3. Surface Modification of Carbon Foam

Figure 18:
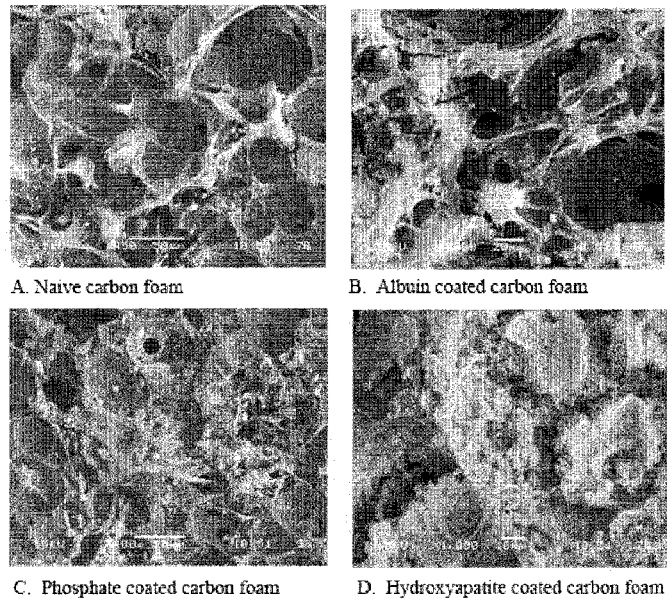
FIG. 18 are SEM images of carbon foam scaffolds with various surface treatments/coatings from Example 3.

Surface modification of the carbon foam scaffold was investigated in a number of cell culture studies using bone marrow derived osteoblasts. Scaffolds were coated with serum albumin, phosphate, and hydroxyapatite. The data (FIG. 18) indicated that cultures of bone marrow-derived osteoblasts on carbon foam scaffolds for 7 days resulted in cells that developed a spindle or polygonal morphology. The cytoplasmatic projections evidently attached to the scaffold so as to facilitate cell adhesion and spread. Extracellular matrix (collagen-like fibers) produced by osteoblasts was clearly present at intercellular regions indicating cell colonization. Optimal cell growth and scaffold pore penetration was obtained on carbon foam scaffolds coated with albumin, suggesting that protein modification improved cell adhesion and colonization. However, cell growth also appeared adequate on uncoated carbon foam and moderate on scaffolds modified by phosphate. Coating with hydroxyapatite at the level applied in this experiment resulted in occlusion of pores within the carbon foam structure, which significantly reduced cell adhesion and surface colonization. Further testing and scaffold pore size modification will be required to optimize carbon foams coated with hydroxyapatite. Evaluation of cell viability using dye exclusion techniques revealed a high level of viability within the cultures, suggesting that hydroxyapatite coating preparations reduced cell attachment rather than exerted a toxic effect upon the cells.

Example 4

In Vivo Biocompatibility of Carbon Foam

Initial in vivo testing of carbon foam scaffolds was carried out to further evaluate the material for biocompatibility and determine if cellular ingrowth within the porous structure could be readily achieved. Two forms of carbon (DUOCEL®) with widely disparate structural properties were selected for testing: (1) A closed cell carbon foam (pore size ~120 µm); and (2) An open cell carbon foam (pore size ~1 mm). Initial testing was conducted using a previously-developed murine air pouch implantation model (Wooley et al. *Inflammatory responses to orthopedic biomaterials in the murine air pouch*. Biomaterials 2002; 23:517-526; and Ottaviani et al. *Inflammatory and immunological responses to hyaluronan preparations. Study of a murine biocompatibility model*. J Bone Joint Surg Am 2007; 89(1):148-157).

Balb/c mice weighing 20-25 g were divided into two implantation groups, and air pouches were established 6 days before carbon foam implantation. An area of the dorsal-lateral skin (2 cm$^2$) was cleaned with alcohol and shaved to provide the pouch site. A subcutaneous injection of 2.5 ml of air was carried out at a single site with a 25-gauge needle and 20 ml syringe. The air pouches were re-injected with 1 ml of air on alternate days for 6 days to establish a fluid-filled pouch beneath the skin. Carbon foam scaffolds (5 mm diameter, 2 mm thick discs) were surgically implanted into the air-pouch through a 1 cm incision, and the mice were observed for any adverse effects of the biomaterial. Animals were sacrificed fourteen days after implantation, and both pouch tissue and the carbon foam scaffolds were recovered for histopathological evaluation.

Figure 19:
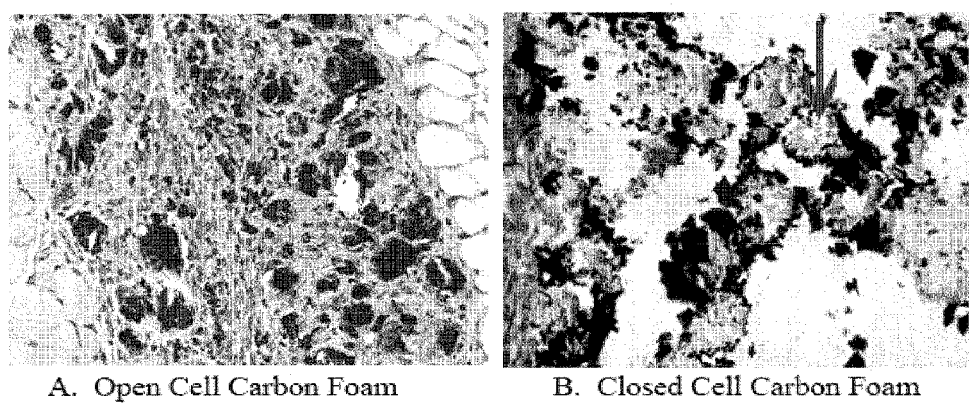
FIG. 19 are photos of hematoxylin & eosin stained sections of recovered implants from Example 4.
Figure 20:
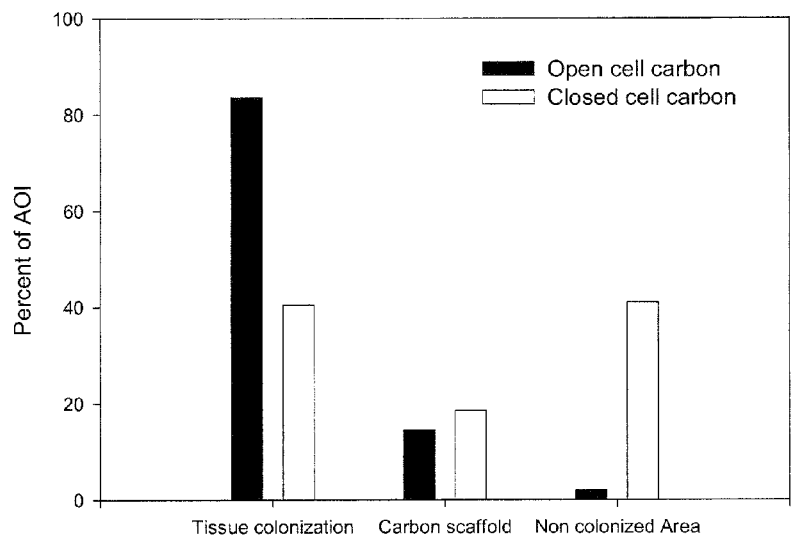
FIG. 20 is a graph comparing the colonization between the open-cell and closed-cell foams from Example 4.

Gross examination of the air pouch indicated a mild to moderate degree of inflammation in response to both forms of carbon foam. Histological examination of the recovered implant sections stained with hematoxylin & eosin (H&E) (FIG. 19) indicated complete fibrous tissue colonization within the open cell carbon foam, and substantial colonization within the closed cell material. Image analysis (FIG. 20) to determine tissue occupancy within the carbon foam scaffold reflected the microscopic appearance, and indicated that 98% of the open cell scaffold was occupied by carbon foam or fibrous tissue, compared with only 49% of the closed cell scaffold. The data indicate that the level of porosity and scaffold pore size exert a strong influence on the level of fibrous tissue ingrowth. However, it appears that neither fibrous tissue ingrowth nor blood vessel formation (see arrow, FIG. 19B) are excluded by a scaffold pore size of approximately 120 µm.

Example 5

Evaluation of Osteoblast Integration into Porous Carbon Foam Matrix

Figure 21:
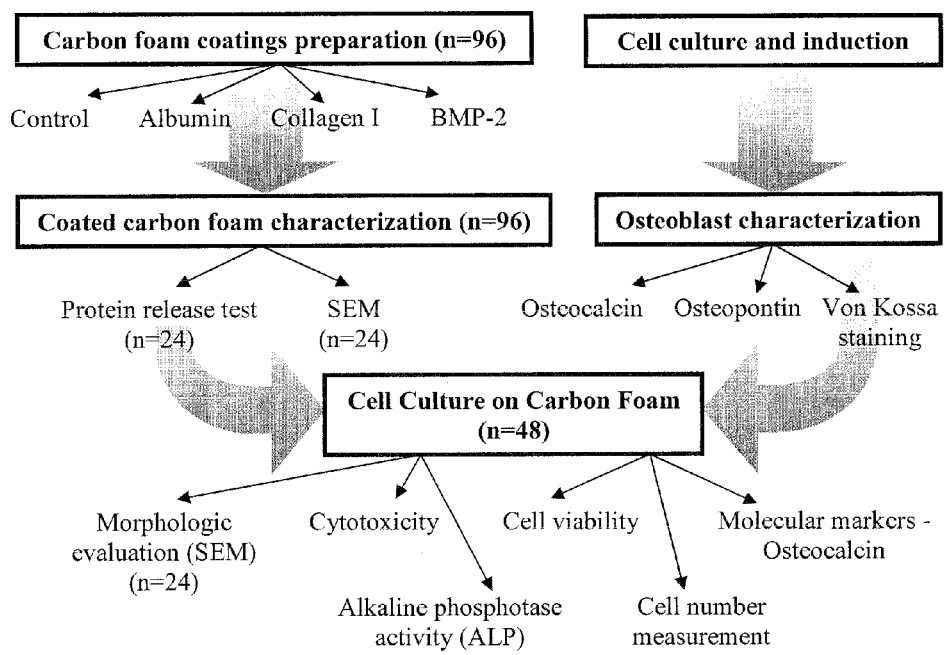
FIG. 21 is a flowchart of the protocol followed in Example 5.

The objective of this study was to examine several factors associated with cell attachment to the surface (osteoblast integration) of the carbon foam scaffold and study the effects of various coatings applied to the carbon foam scaffold. A flowchart of the study protocol is shown in FIG. 21.

1. Materials and Methods

Reticulated vitreous carbon foam (DUOCEL® RVC carbon foam; ERG Materials and Aerospace Corporation, Oakland, Calif.) with 80 PPI, 3% relative density and pore sizes ranging from 40-250 µm was used for these experiments. Four different types of carbon foam conditions were examined: (A) Original (uncoated) carbon foam; (B) Albumin-coated carbon foam; (C) Collagen type I-coated carbon foam; and (D) Bone Morphogenetic Protein 2 ("BMP-2") coated carbon foam. The original (uncoated) carbon foam sample group was selected as the baseline for comparison of the other sample groups. A total of ninety six discs (24 for each sample group) were machined and cut into 1-cm diameter and 2-mm thick cylinders. The discs were cleaned with alcohol to remove residual carbon dust from machining.

2. Carbon Foam Coatings Preparation

The discs were subjected to one of 3 pretreatments: (1) immersion in 10 µg/ml human serum albumin (HSA) with distilled water for 24 hours at 37° C.; (2) immersion in collagen type 1 solution for 24 hours at 37° C.; or (3) immersion in 10 µg/ml BMP-2 with distilled water for 24 hours at 37° C. Carbon foam discs immersed in distilled water served as a control. A low pressure vacuum system was used to facilitate the absorption of the coatings into the pores inside the carbon foam discs. The treated carbon foams were then carefully centrifuged to remove excessive solution. All samples were then air-dried in a biology hood overnight. Residual pretreatment solutions were collected and measured for albumin, collagen I, or BMP-2 concentration using an enzyme-linked immunosorbent assay (ELISA).

3. Coated Carbon Foam Characterization a. In vitro Protein Release Test:

Coated carbon foam discs (6 samples/group) were placed in a 24-well plate with 1 ml of phosphate buffer solution (PBS) with pH 7.4 release buffer. The carbon foam discs were then incubated at 37° C., the release buffer was collected and replaced with fresh buffer daily for 6 days. All samples were then stored at −20° C. until analysis. The albumin, collagen type I or BMP-2 released from the samples was then assayed using ELISA. Duplicate series of 8 two-fold dilutions of each coated material ranging from 1,000 to 4 ng/ml were prepared, and this served as a standard data set to determine protein concentrations of the sample groups. The absorbance of the samples and standards were measured at 450 nm wavelength using a microtiter plate reader, and the cumulative release of albumin, collagen type I or BMP-2 was extrapolated from the standard curves.

b. Scanning Electron Microscopy (SEM)

All the samples were mounted onto SEM stubs, and the porous properties of the carbon foam (SEM images) were observed and evaluated at 10 kV or 15 kV using a scanning electron microscope.

4. Cell Culture and Induction

Bone marrow cells (BMC) were obtained from the bone marrow of female Lewis rats. Following euthanasia by $CO_2$ asphyxiation, femora were aseptically excised, the metaphyseal ends were cut off and the marrow was flushed from the medullary cavity with 10 ml of Dulbecco's Modified Eagle medium (DMEM) using a syringe with a 22-gauge needle. Cell clumps were dispersed by repeatedly pipetting the cell suspension, and low-density bone marrow mononuclear cells isolated using density centrifugation over Histopaque®-1083. Cells were then washed with PBS, and prepared for culture and differentiation of osteoblasts. BMCs were induced to differentiate into osteoblasts in complete media consisting of DMEM supplemented with 10% fetal bovine serum (FBS), 10 mM β-glycerol phosphate, 100 µM L-ascorbic acid, and 10 nM dexamethasone, 2 mM glutamine, 100 U/ml penicillin, 100 ug/ml streptomycin, and $10^{-4}$ M L-ascorbic acid. The induced BMCs were then seeded on the coated carbon foam discs and cultured in an incubator at 37° C. for seven days.

5. Osteoblast Characterization a. Osteocalcin, Osteopontin, and Collagen Type I

On the second passage, the induced osteoblasts were fixed in 4% paraformaldehyde, permeated with 0.01% Triton X-100 in PBS, and incubated in 1% block serum for 1 hour at 37° C. The cells were then incubated with anti-osteocalcin, osteopontin, or collagen type I for 1 hour, and visualized using Alexa Fluor conjugated (Molecular Probes, Eugene, Oreg.) (for osteocalcin and osteopontin) or Alexa Fluor 488-conjugated (Molecular Probes, Eugene, Oreg.) (for collagen type I) secondary antibody. The cells were examined under a fluorescence microscope. Nuclei were counterstained with DAPI (Molecular Probes, Eugene, Oreg.).

b. Von Kossa Staining

The presence of calcium deposits was demonstrated by von Kossa staining. Potential osteoblasts were rinsed in PBS and fixed in 4% paraformaldehyde for 30 minutes, and then incubated with 1% silver nitrate solution (Sigma-Aldrich, US) under ultraviolet light for 20 minutes. Un-reacted silver was removed by 5% sodium thiosulfate (Sigma-Aldrich, US) for 5 minutes. The stained slides were then observed under microscope after permanent mounting.

6. Cell Culture on Carbon Foam

Induced osteoblasts in 50 μl suspensions ($3.5 \times 10^6$ cells/ml) were respectively loaded onto each scaffold in 24-well plates. The scaffolds were left undisturbed in a 37° C. incubator for 2 hours to allow cells to attach to the scaffold, after which the seeded cells on materials were kept in culture using the same osteogenic media. Medium was changed every 3 days, and at Day 7 samples were harvested for morphological and biochemical evaluation. Culture dish cells were used as the control.

7. Morphological Evaluation

To prepare for SEM examination, membranes with Day 7 culture cells were fixed with 2% glutaraldehyde for 60 minutes at 4° C. The samples were then washed twice in PBS and exposed to 2% osmium tetroxide for 60 minutes. Once the samples had been rinsed in distilled water, they were dehydrated through a graded series of ethanol (20%, 40%, 60%, 80%, 95%, and 100%) for 5 minutes. The dehydration process was completed in hexamethyl di silazane (HMDS) for 10 minutes. After air-drying, the samples were spot-coated with gold and mounted onto SEM stubs. SEM images were observed at 10 kV or 15 kV, and saved for the morphology evaluation of the induced osteogenic cells on the scaffolds.

8. Cytotoxicity

Cytotoxicity of carbon foams was quantitatively assessed by the measurement of lactate dehydrogenase (LDH) leakage. A CytoTox 96® assay was used to measure the ratio of lifeless cell to live cells on the bone or composite scaffold. LDH is an outstanding indicator of cell death and damage. Lifeless cells release LDH during culturing, therefore, it is essential to collect the cultured medium along with the lysis buffer supernatant. 10 μl of aliquots of the medium was mixed with 200 μl LDH reagent, and the cultured medium and lysis buffer solutions for each of the four groups were transferred to their corresponding well. A spectrophotometer (Spectra MAX Gemini XS) was used to measure the absorbance of solutions at 490 nm wavelength. Higher readings correspond to a higher toxic environment for osteogenic cells.

9. Cell Viability

Cell viability was assayed by analyzing the mitochondrial activities in the cultured cells on the discs. The alamarBlue® assay (BioSource, US) was used to determine the activity of the cells after 7 days of cell culture. AlamarBlue® reagent is a valuable tool used to ensure cell proliferation on the discs through correlating cell number to the absorbance values. In contrast to cytotoxicity tests, the cultured medium was removed completely with PBS and fresh medium was added to cover the composite samples. 3 ml of new conditioned media supplemented with 200 μl of alamarBlue® was added to each well, and incubation was continued at 37° C. with 5% $CO_2$ for 4 hours. The culture medium was then transferred to a 96-well plate and read on a spectrophotometer (Spectra MAX Gemini XS) at excitation wavelength 570 nm, emission wavelength 600 nm, and data was collected and analyzed using SoftMax PRO. The alamarBlue® absorbance of DNA values were calculated for each sample.

10. Cell Number Measurement

Cell numbers were determined by a fluorometric quantification of DNA on the carbon foam construct. After the alamarBlue® assay, the cell-scaffolds were rinsed with PBS, followed by 1 ml lysis buffer and 2 minutes ultrasonic. The lysate was then saved into a specific tube. 100 μl of supernatant sample were mixed in 1.5 ml of 200 ng/ml Hoechst 33258 fluorescent dye (Sigma-Aldrich, US) and read at EX 350 nm and EM 455 nm by fluorometer. The DNA concentration in the samples was determined against a DNA standard curve.

11. Alkaline Phosphatase (ALP) Activity

ALP activity by osteogenic cells was measured using a spectrophotometer. After the previous freeze-thaw cycle (freeze at −80° C. for 30 minutes, and thaw at 37° C. for 30 minutes) and homogenization for the DNA assay, 100 μl of the sample was removed from the lysate to which 100 μl of p-nitrophenyl phosphate solution was added. After 30 minutes incubation at 37° C., the production of p-nitrophenol in the presence of ALP was measured at an absorbance of 405 nm wavelength. The measurement of the ALP assay was normalized against the amount of total DNA in each sample.

12. Molecular Markers (Osteocalcin)

Cell lysates were used for the assay of osteocalcin using a sandwich ELISA. 2 μg/ml of primary antibody was coated and incubated overnight at 4° C. The plates were washed 3 times with PBS, dispensed with 200 μl of 5% milk and incubated at 37° C. for 4-6 hours. Samples with 50 μl of supernatant were added to the coating plate and incubated overnight at 4° C., followed by washing the plate and adding 100 μl of 1 μg/ml antibody, followed by incubating at 37° C. for 1 hour. Plates were washed and then 20 μl of streptavidin was added into 10 ml of PBS, and incubated at 40° C. Next, 2 pNPP was dissolved per 10 ml of diethanolamine buffer, followed by incubation at 37° C. in the dark for 5-20 minutes. A spectrophotometer (Spectra MAX Gemini XS) was used to measure the absorbance of solutions at 405 nm wavelength, and the absorbance of ELISA was normalized against the amount of total DNA in each sample.

13. Results a. Characterization of Coated Carbon Foam (1) Protein Release Test

Figure 22:
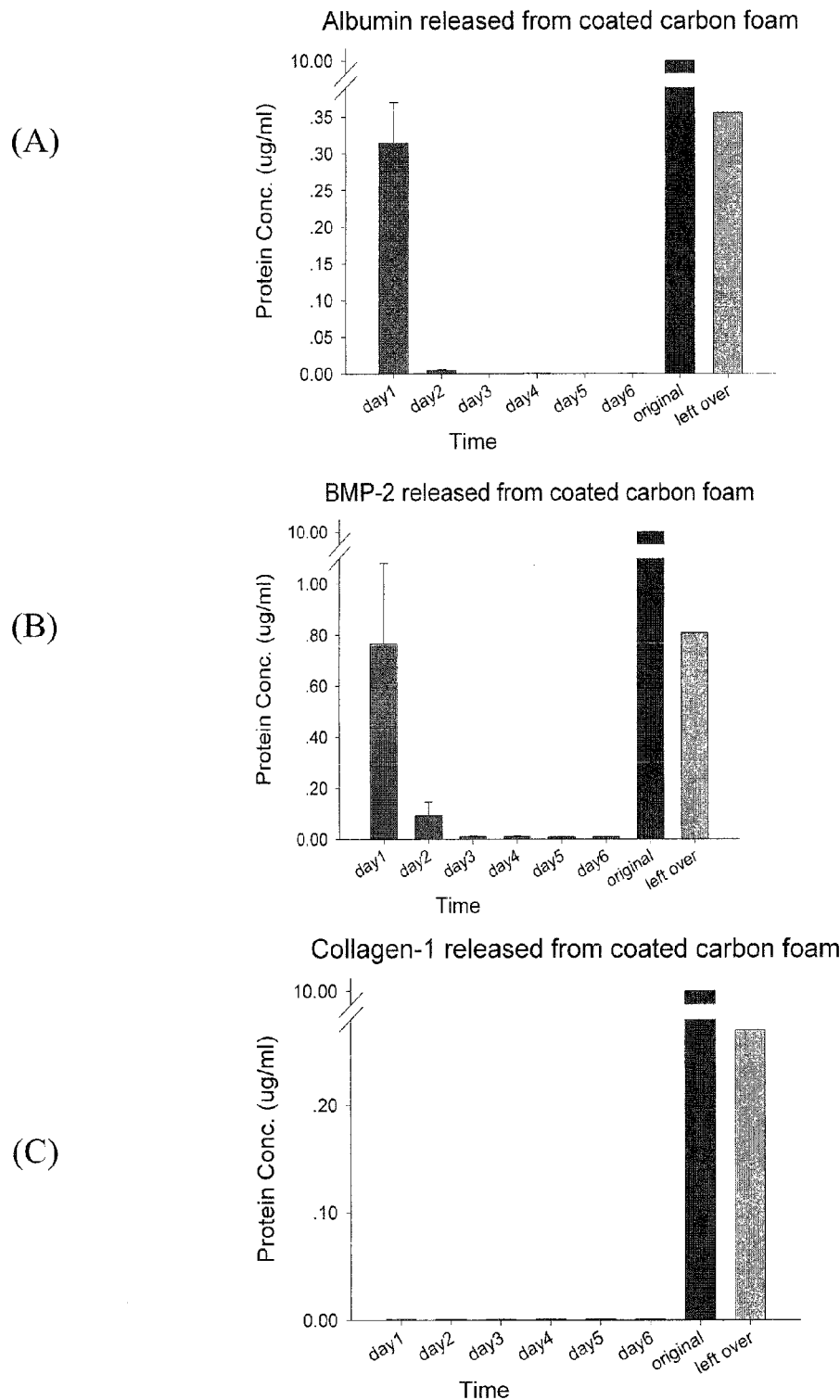
FIG. 22(A)-(C) shows charts for protein release assays from Example 5.

Both albumin and BMP-2 exhibited a minimal burst release in the first 24 hours with the albumin and BMP-2 releasing 0.108% and 0.2733%, respectively (FIG. 22A-B). These burst releases were followed by significantly reduced release rates thereafter. Collagen type I did not exhibit the same burst release profile as seen with albumin and BMP-2 in the first 24 hours (FIG. 22C). Collagen type I was released steadily at the rate of 0.0003% during 6 days of assessment. This negligible release of collagen type I from the carbon foam allowed a high retention of protein on the surface of the biomaterial, which subsequently contributed to its biological effect on attached cells. While the cumulative releases of albumin and BMP-2 from carbon were more than that of the collagen type I, the retentions of albumin and BMP-2 still were up to 99.89% and 99.68%, respectively. Therefore, it is possible that the minimal release rates have allowed sufficient amounts of albumin and BMP-2 to remain, and then sustain cell adhesion, proliferation, and the formation of bony matrix afterward. The stable and long retention of protein on the scaffold will allow for the increase of release duration and the local protein concentration. This pattern of release may rarely lead to a distant spread of the protein, and subsequent ectopic bone formation.

Collagen type I and H₂O treated carbon foams led to higher cell viability than the albumin and BMP-2 groups, which were represented by the alamarBlue® reading normalized by

TABLE 2

Protein release from coated carbon foam

| | Albumin | | BMP-2 | | Collagen type I | |
|---|---|---|---|---|---|---|
| | Concentration (μg/ml) | Rate (%) | Concentration (μg/ml) | Rate (%) | Concentration (μg/ml) | Rate (%) |
| Day 1 | 0.31510 ± 0.05510 | 0.1081 | 0.76700 ± 0.31370 | 0.2733 | 0.00074 ± 0.00002 | 0.0003 |
| Day 2 | 0.00442 ± 0.00122 | 0.0015 | 0.09230 ± 0.05300 | 0.0329 | 0.00074 ± 0.00005 | 0.0003 |
| Day 3 | 0.00061 ± 0.00007 | 0.0002 | 0.01080 ± 0.00105 | 0.0038 | 0.00071 ± 0.00001 | 0.0002 |
| Day 4 | 0.00084 ± 0.00008 | 0.0003 | 0.01100 ± 0.00118 | 0.0039 | 0.00069 ± 0.00002 | 0.0002 |
| Day 5 | 0.00070 ± 0.00002 | 0.0002 | 0.01020 ± 0.00082 | 0.0036 | 0.00069 ± 0.00003 | 0.0002 |
| Day 6 | 0.00076 ± 0.00010 | 0.0003 | 0.00957 ± 0.00025 | 0.0034 | 0.00072 ± 0.00004 | 0.0002 |
| Original | 10.00000 | | 10.00000 | | 10.00000 | |
| Left over | 0.35570 | | 0.80780 | | 0.26970 | |

The percent release of protein at each time point was determined as follows:

$$\text{Release Rate} = \frac{\text{amount of protein released at day } X}{\left(\dfrac{50\ \mu g \text{ protein} - }{\text{amount of protein left over}}\right) / 6 \text{ samples}} \times 100\%$$

b. Osteoblast Characterization

Figure 23:
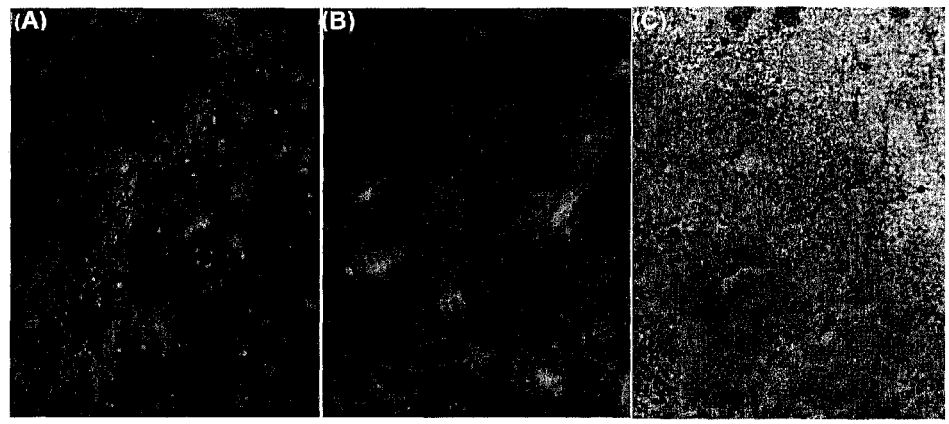
FIG. 23 shows images from the immunocytofluorescence test in Example 5.

The capacity of the induced osteoblasts to express osteocalcin, osteopontin, and collagen type I was examined by immunocytofluorescence (FIG. 23). While the expression of osteocalcin (in red, FIG. 23A) and osteopontin (in red, FIG. 23B) was prominent in the induced osteoblasts, these cells were further identified by positive staining for collagen type I (in green, FIG. 23A-B), indicating that the induced cells possessed the distinguishable osteoblastic phenotype. To demonstrate the ability of cells to mineralize the matrix, cells cultured on Petri dishes were subjected to von Kossa staining to reveal calcium deposition (FIG. 23C). The darkly stained mineralized nodules were visualized by silver nitrate, indicating normal osteoblast function in conditioned culture.

TABLE 3

Cell culture on carbon foam

| | alamarBlue ® (OD/ug DNA) | ALP (OD/ug DNA) | Osteocalcin (ng/ug DNA) | LDH |
|---|---|---|---|---|
| Albumin | 0.007 ± 0.003 | 0.005 ± 0.003 | 0.039 ± 0.023 | −0.951 ± 1.041 |
| BMP-2 | 0.010 ± 0.001 | 0.006 ± 0.002 | 0.028 ± 0.011 | 1.491 ± 1.126 |
| Collagen I | 0.015 ± 0.001 | 0.008 ± 0.003 | 0.065 ± 0.045 | 1.829 ± 1.961 |
| H₂O | 0.015 ± 0.002 | 0.009 ± 0.002 | 0.018 ± 0.013 | 0.520 ± 0.786 |

Figure 24:
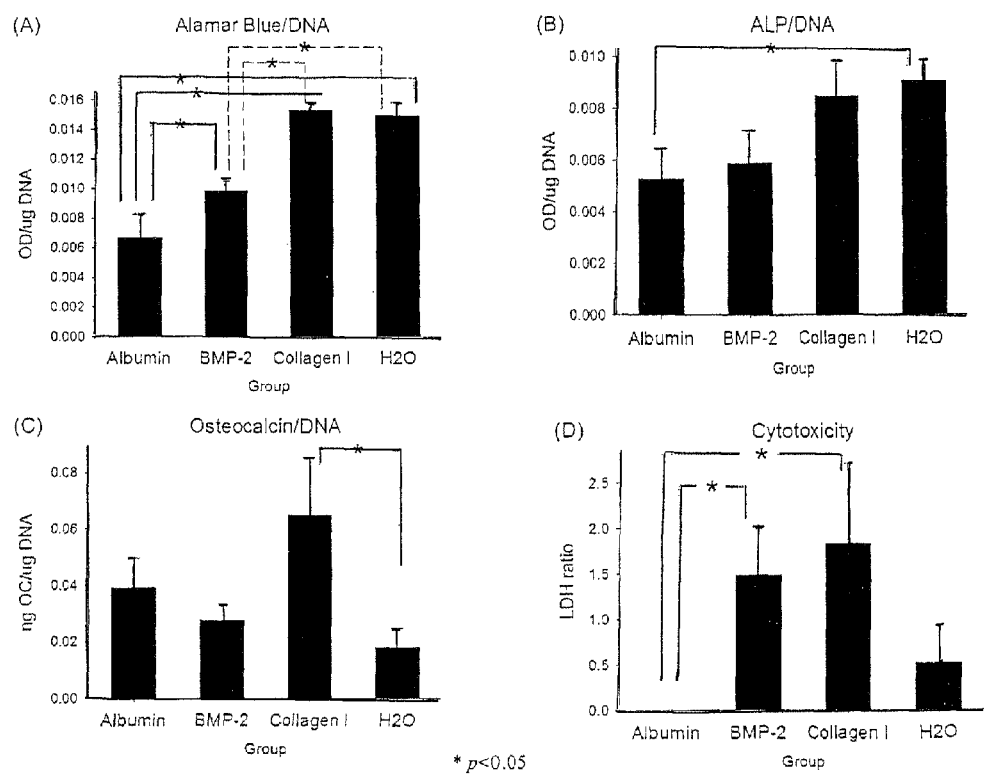
FIG. 24 shows charts for the effects of different protein coatings on osteoblasts from Example 5.

To test the effects of different protein coatings on osteoblasts, we analyzed cell viability, ALP activity, osteocalcin expression, and cell damage of osteoblasts using spectrophotometry or spectrofluorometry at the single-cell level by culturing cells on carbon foam in vitro for 1 week. Relative quantification of activities at the single-cell level was employed in this study, because augmented cellular functions and viabilities should definitely be pursued when cell amounts could be controlled relatively easily as assembling engineered bone. Comparisons were made among the groups of albumin, BMP-2, collagen type I, and H₂O treated carbon foams (FIG. 24).

DNA amount in each group. ALP activity and osteocalcin expression are functional and maturational indicators of the osteoblast phenotype, and partially correlated with capacity of bone formation. It seemed that the ALP activity responded to varying materials in a similar way to cell viability, with the higher values for ALP observed at the groups of collagen type I and H₂O. Compared with the other groups, the collagen type I stimulated higher osteocalcin expression, although the statistical significances were obscure with the exception of collagen type I vs. H₂O. BMP-2, the well-known osteogenic protein which has been widely used in bone reconstructive surgery, was expected to facilitate the osteoblast differentiation and function. In the current study, however, BMP-2 appeared not to provide a more favorable environment for osteoblast function, which was observed as the lower production of ALP and osteocalcin. Paradoxically, collagen type I and BMP-2 treated carbon foam led to an apparent cytotoxicity, which was indicated by a higher reading of the LDH ratio. It is difficult to interpret the concurrent promoting and inhibiting effect of collagen type I on the osteoblasts, which were evidenced by the higher readings in the alamarBlue® and LDH assays. The albumin group, however, exhibited the lowest cell viability (i.e., alamarBlue®/DNA) as well as the lowest adverse effect on the cells (i.e., LDH). In contrast, H₂O-treated carbon foam, with the absence of any protein coating, demonstrated promising properties: higher cell viability, lower cell toxicity, and higher ALP activity, with the exception of the lower osteocalcin production.

Example 6

Subsidence Testing

In this Example, the efficacy of intervertebral fusion devices for the lumbar spine was examined. The implants tested were of sizes representing small to medium lumbar ALIF designs. There are four specimen designs (shapes) with two wall thicknesses and one specimen design with one wall thickness for a total of 9 variable designs.

1. Procedure/Methodology a. Specimen Fabrication

Due to the complication in manufacturing these implants using PEEK, and keeping the time scale in perspective, preliminary investigation to determine efficacy of implant design, the testing was conducted on implants fabricated using the 3-D printer. The implants were manufactured from ULTEM 9085. The test results do not establish ultimate strength but rather comparative performance of the various possible implant shapes. The testing was conducted with these specimens mounted on grade 15 polyurethane blocks already obtained for this phase of the project.

b. Testing

Testing to determine the subsidence levels for the spinal implants was carried out as closely as possible per ASTM F2267-04. Preliminary testing was carried out using fixtures designed for this activity. The fixtures were made of ULTEM 9085 material. The fixtures were designed specifically for use at ORI laboratory MTS 22 Kip axial/torsion load frame.

Special care was exercised in tightening the fixture onto the load frame, and washers were used during fastening to prevent damage to the ULTEM fixture. The fixture was designed with the lordotic angle built in to allow for easier specimen set up. The specimen was placed using an alignment jig to make certain that the load point passed through the geometric center of the implant. Table 4 shows the testing conducted to determine the implant stiffness of the 5 implant designs. Table 5 lists the second testing variable—subsidence of the implant types.

TABLE 4

Testing to Determine Spinal Implant Stiffness ($K_d$)

| Specimen Type/Shape* | Wall thickness | No. of Specimens |
|---|---|---|
| A | 3.75 & 5.00 mm | 6 (3 per thickness) |
| B | 3.75 & 5.00 mm | 6 (3 per thickness) |
| C | 3.75 & 5.00 mm | 6 (3 per thickness) |
| D | 3.75 & 5.00 mm | 6 (3 per thickness) |
| E | NA | 3 |
| Total number of implants | | 27 |

Figure 25:
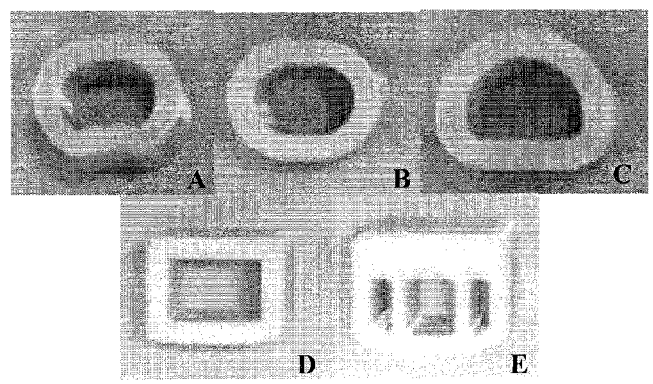
FIG. 25 shows photographs of the implant shapes tested in Example 6.

*FIG. 25 shows photographs of the various implant shapes tested in this Example.

Loading for both implant stiffness and subsidence were conducted at a rate of 0.1 mm/s. The load displacement data from the results of testing from Table 4 was used to determine $K_d$ (Implant Stiffness) and the experimental results of Table 5 were used to determine $K_s$ (Total System Stiffness). Equation 1 was then used to determine the Average Foam Stiffness ($K_p$). The value of the average Foam Stiffness was then used as the basis for comparison of the different implant types and thicknesses.

$$Kp = \frac{Ks * Kd}{Kd - Ks} \quad \text{Eq. 1}$$

Testing was conducted as recommended in ASTM F2267-04. The results were evaluated as per Appendix of the same. For and additional information ASTM F2267 & F2077 should be consulted.

TABLE 5

Testing to Determine Propensity to Subside

| Specimen Type | Wall thickness | No. of Specimens |
|---|---|---|
| A | 3.75 & 5.00 mm | 6 (3 per thickness) |
| B | 3.75 & 5.00 mm | 6 (3 per thickness) |
| C | 3.75 & 5.00 mm | 6 (3 per thickness) |
| D | 3.75 & 5.00 mm | 6 (3 per thickness) |
| E | NA | 3 |
| Total number of specimens | | 27 |

2. Results a. Implant Stiffness ($K_d$) Testing

Figure 26:
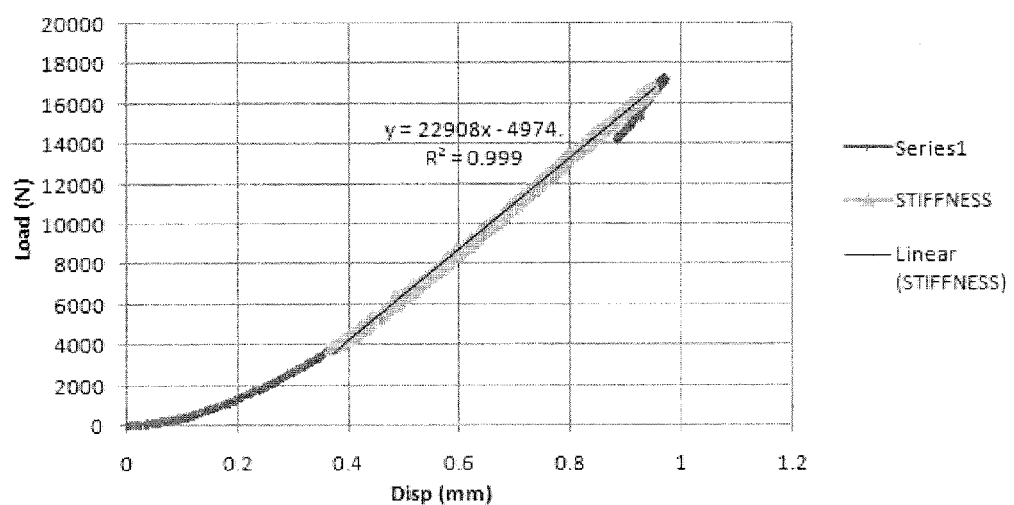
FIG. 26 is a graph of a Load-Displacement Curve for Implant Stiffness Testing from Example 6.

During each compression test used to determine the implant stiffness, load, displacement, and time data was collected. From this data, load-displacement graphs were generated, as seen in FIG. 26. The stiffness of each implant was determined by calculating the slope of the linear portion of the load-displacement curve. The $R^2$ values for each slope used were between 0.994 and 0.999, ensuring that the linear approximation of each curve was a good representation of the dataset.

Figure 27:
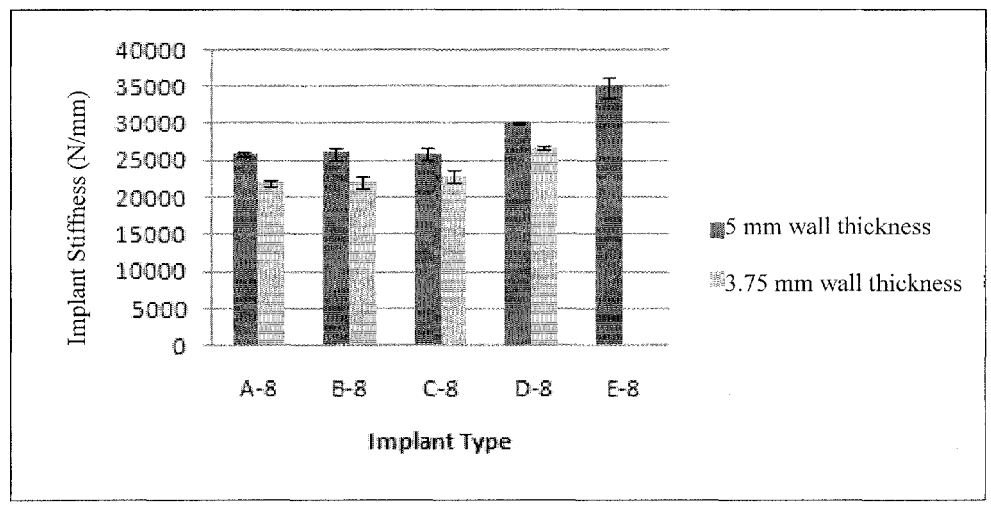
FIG. 27 is a graph of the Implant Stiffness ($K_d$) Values from Example 6.

The average stiffness values for each implant with their standard deviations are shown in FIG. 27. As a rule, the implants with thinner wall thicknesses also had lower implant stiffness. The standard deviations for all average implant stiffness were within reasonable values, as is seen on the graph below. The average implant stiffness for implant type E-8 was the highest (34991 N/mm), while implant A-8-3.75 had the lowest average stiffness (21948 N/mm) Implants B-8-3.75 (22166 N/mm) and C-8-3.75 (22780 N/mm) also displayed very low values of implant stiffness. Mean stiffness values for each implant type and wall thickness are shown in Table 6.

TABLE 6

Implant Stiffness ($K_d$) in N/mm

| | A-8-5 | A-8-3.75 | B-8-5 | B-8-3.75 | C-8-5 | C-8-3.75 | D-8-5 | D-8-3.75 | E-8 |
|---|---|---|---|---|---|---|---|---|---|
| Mean | 25915 | 21948 | 25990 | 22166 | 25897 | 22780 | 30187 | 26736 | 34991 |
| SD | 305 | 813 | 811 | 213 | 1379 | 164 | 445 | 1396 | 1939 |
| Min | 24933 | 20920 | 25068 | 21950 | 24307 | 22591 | 24688 | 25903 | 32651 |
| Max | 26265 | 22908 | 26309 | 22376 | 26605 | 22868 | 30693 | 28348 | 37307 | b. Total System Stiffness ($K_s$) Testing

Figure 28:
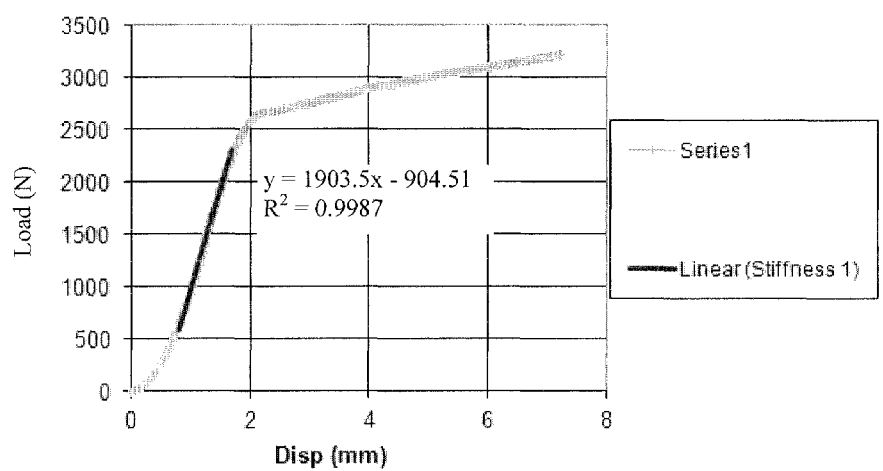
FIG. 28 is a graph of a Load-Displacement Curve of Total System Stiffness Testing from Example 6.
Figure 29:
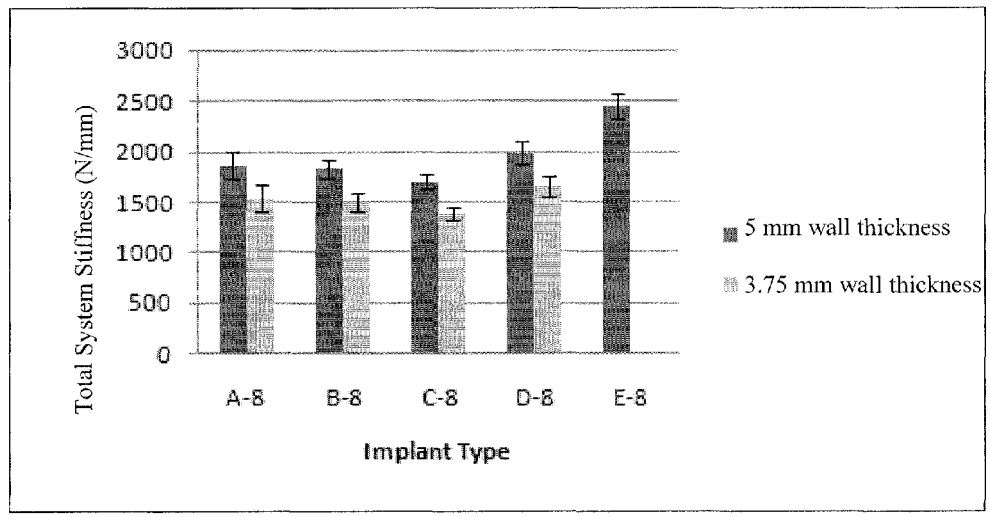
FIG. 29 is a graph of the Total System Stiffness ($K_s$) in N/mm from Example 6.

During each compression test used to determine the total system stiffness, load, displacement, and time data was collected. From this data, Load-Displacement graphs were generated, and the stiffness of the whole system was calculated (FIG. 28). The first linear portion of the L-D curve was used to calculate the system stiffness per ASTM the standard. All $R^2$ values were calculated to be between 0.994 and 0.999. The results for the Total System Stiffness are shown in FIG. 29. Again, the maximum stiffness was seen while testing implant E-8 (2453 N/mm). The minimum stiffness was calculated from the test that occurred with implant C-8-3.75 (1382 N/min). The second lowest stiffness value was calculated from specimen B-8-3.75 (1498 N/mm). The reduced data from the Total System Stiffness test is displayed below in Table 7.

TABLE 7

Total System Stiffness ($K_s$) in N/mm

|      | A-8-5 | A-8-3.75 | B-8-5 | B-8-3.75 | C-8-5 | C-8-3.75 | D-8-5 | D-8-3.75 | E-8  |
|------|-------|----------|-------|----------|-------|----------|-------|----------|------|
| Mean | 1857  | 1535     | 1833  | 1498     | 1699  | 1382     | 1985  | 1651     | 2453 |
| SD   | 132   | 93       | 67    | 110      | 119   | 98       | 264   | 55       | 193  |
| Min  | 1708  | 1448     | 1772  | 1376     | 1569  | 1263     | 1798  | 1601     | 2235 |
| Max  | 1960  | 1633     | 1906  | 1598     | 1840  | 1497     | 2171  | 1704     | 2604 | c. Average Foam Stiffness ($K_p$)

The values for average foam stiffness were calculated using Equation 1. The results from these calculations are displayed in FIG. 30, and are tabulated in Table 8. The bars shown for each implant type on FIG. 30 display the ranges of Average Foam Stiffness when calculated with the minimum and maximum values for the Implant Stiffness and the Total System Stiffness. Table 8 displays the calculated average foam stiffness as well as minimum and maximum foam stiffness values for each implant type.

TABLE 8

Average Foam Stiffness ($K_p$) in N/mm

|     | −5   | Min  | Max  | −3.75 | Min  | Max  |
|-----|------|------|------|-------|------|------|
| A-8 | 2000 | 1834 | 2118 | 1651  | 1556 | 1758 |
| B-8 | 1972 | 1907 | 2055 | 1606  | 1468 | 1721 |
| C-8 | 1818 | 1677 | 1977 | 1472  | 1338 | 1977 |
| D-8 | 2124 | 1939 | 2336 | 1759  | 1706 | 1813 |
| E-8 | 2638 | 2399 | 2799 |       |      |      | mance in resisting subsidence. Low foam stiffness values indicate more propensity for the implant to subside.

Figure 30:
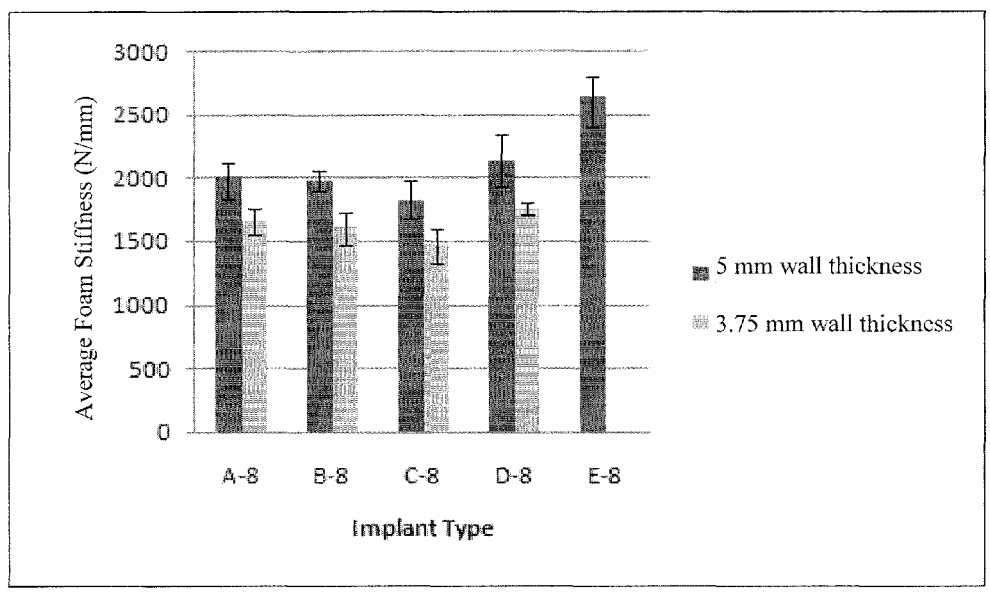
FIG. 30 is a graph of the Average Foam Stiffness (Kp) in N/mm from Example 6.

Two trends are noted when FIG. 30 is examined. First, the implant stiffness does change with implant type, although four of the five implant types have stiffness values close to 2000 N/mm for implants with a 5 mm wall thickness. The second trend noted is that the stiffness values for every implant type decrease with a decrease in wall thickness. In fact, with a 25% decrease in wall thickness, the average foam stiffness ($K_p$) was seen to decrease between 17.2-19.1% for all implant types. This was expected because a decrease in wall thickness decreases the load bearing area, creating higher material stresses. When the material was compressed, the smaller amount of material in contact was not able to react with as large of a force. The smaller load response of the material to the imposed deflection defines a lesser stiffness.

Implant E-8 has a much higher stiffness because it has a larger contact area and less open area within the interior of the device (see Table 4). The shape of implant A is similar to existing devices on the market. Devices B, C, and D were designed with the same footprint as device A but with differing shapes, contact areas, and interior areas. According to the trends seen in FIG. 30, Devices B and C have slightly lower performances (1972 N/mm and 1818 N/mm) than device A (2000 N/mm), while device D (2124 N/mm) has a slightly higher performance.

TABLE 9

A Comparison of $K_p$, Contact Area, and Interior Area

|     | Average Foam Stiffness (Kp) | | | Contact Area | | | Interior Area | | |
|-----|------|-------|------------|--------|-----------|------------|--------|-----------|------------|
|     | −5   | −3.75 | % Decrease | 5 mm²  | 3.75 mm²  | % Decrease | 5 mm²  | 3.75 mm²  | % Increase |
| A-8 | 2000 | 1651  | 17.5       | 363.5  | 287.3     | 20.9       | 233.3  | 309.4     | 32.6       |
| B-8 | 1972 | 1606  | 18.6       | 358.5  | 283.6     | 20.9       | 237.9  | 312.8     | 31.5       |
| C-8 | 1818 | 1472  | 19.1       | 362.1  | 286.3     | 20.9       | 232.8  | 308.5     | 32.6       |
| D-8 | 2124 | 1759  | 17.2       | 427.2  | 336.9     | 21.1       | 279.2  | 369.5     | 32.3       |
| E-8 | 2638 | —     | —          | —      | —         | —          | —      | —         | —          |

3. Discussion

The results found in the calculation of the Average Foam Stiffness ($K_p$) are of primary importance in this experiment. While the results for Implant Stiffness and Total System Stiffness were documented for transparency, the only deciding factor in this experiment is the performance of the implants according to their average foam stiffness. A high Average Foam Stiffness value would indicate better perfor- When comparing the performances of the shape of implant with differing wall thicknesses, it is noted that the average decrease of foam stiffness for a 25% decrease in wall thickness (5 mm to 3.75 mm) was close to 18% (see Table 9). For best subsidence performance of implants with a decreased wall thicknesses, the foam stiffness decrease should be minimized. The decrease in contact area (implant load bearing area) was close to 21%, and the increase in internal area was near 32%.

To the extent possible, the percent decrease of foam stiffness should be minimized and the percent increase of interior area should be maximized. In Table 10, the difference of the two values was calculated (Interior Area—Stiffness). A high difference value indicates the best relationship between an increase in interior surface area and a small decrease in stiffness when the wall thickness was decreased 25%. Under these conditions, implant types A and D have the best relationship between retaining a large interior area and a small decrease in stiffness when wall thickness is reduced.

TABLE 10

Performance Matrix

|  | % Decrease in Stiffness | % Increase in Interior Area | Difference |
|---|---|---|---|
| A-8 | 17.5% | 32.6% | 15.2% |
| B-8 | 18.6% | 31.5% | 12.9% |
| C-8 | 19.1% | 32.6% | 13.5% |
| D-8 | 17.2% | 32.3% | 15.2% |

We claim:

1. An intervertebral implant comprising:
    a cage comprising:
        a superior surface, an inferior surface, and an outer wall extending between the superior surface and inferior surface, said outer wall comprising an exterior surface defining the outer perimeter of said implant, and an interior surface defining an inner space; and
    a porous core received within said inner space, said core comprising a carbonaceous matrix comprising a continuous phase having a surface and defining a plurality of open spaces throughout said matrix; and a coating immobilized and adsorbed on said continuous phase surface of said matrix, said coating being selected from the group consisting of osteopromotive materials, therapeutic agents, and combinations thereof.

2. The implant of claim 1, wherein said porous core consists essentially of said carbonaceous matrix and said coating.

3. The implant of claim 1, wherein said coating is an osteopromotive material or therapeutic agent selected from the group consisting osteoconductive materials, osteoinductive materials, small molecule drugs, biologics, and combinations thereof.

4. The implant of claim 1, wherein said matrix is formed of a carbonaceous material selected from the group consisting of carbon foam, graphitic foam, and combinations thereof.

5. The implant of claim 1, wherein said open spaces comprise pores in said matrix, said matrix comprising an open cell structure having a plurality of interconnected pores throughout said matrix.

6. The implant of claim 1, wherein said implant is substantially free of metals.

7. The implant of claim 1, wherein said cage is formed of carbon fiber reinforced polymer.

8. The implant of claim 1, wherein said implant has an anterior portion and a posterior portion, having respective heights, wherein the height H of said implant at said anterior portion is greater than the height h of said implant at said posterior portion.

9. A method of replacing an intervertebral disc in an interbody space between first and second vertebral bodies of a subject, said method comprising:
    providing an intervertebral implant according to claim 1;
    shaping said porous core to yield a void;
    packing said void with a bone grafting material; and
    implanting said implant into said interbody space of said subject between said first and second vertebral bodies.

10. The method of claim 9, wherein said porous core comprises: a superior surface region and an inferior surface region, wherein said superior surface region and said superior surface of said cage cooperatively define a superior face of said implant, said superior face being configured to contact said first vertebral body after said implanting, and wherein said inferior surface region and said inferior surface of said cage cooperatively define an inferior face of said implant, said inferior face being configured to contact said second vertebral body after said implanting.

11. The method of claim 10, wherein said void is an axial hole extending between said superior surface region and said inferior surface region of said porous core, and wherein said shaping comprises drilling said axial hole through said porous core.

12. The method of claim 10, wherein said void is a depression, and wherein said shaping comprises foaming said depression in said superior surface region, said inferior surface region, or a combination thereof.

13. The method of claim 9, wherein said shaping occurs immediately prior to said packing.

14. A kit for use in replacing an intervertebral disc in an interbody space between first and second vertebral bodies of a subject, said kit comprising:
    an intervertebral implant according to claim 1; and
    instructions for the implantation thereof into said subject.

15. The kit of claim 14, further comprising:
    instructions for shaping said porous core to form a void for packing bone grafting material into said core; and
    optionally, one or more tools for the shaping thereof.

16. The implant of claim 1, wherein said osteopromotive materials and/or therapeutic agents are tightly bound to said carbonaceous matrix and retain their bioavailability after implantation in a subject.

17. The implant of claim 1, wherein said coating is not covalently or chemically bonded to said carbonaceous matrix.

18. The implant of claim 1, wherein said open spaces comprise pores in said matrix, said matrix having an average pore diameter of at least 50 μm.

19. The implant of claim 1, wherein said carbonaceous matrix is vitreous carbon foam.

* * * * *